United States Patent [19]

Nakagawa et al.

[11] Patent Number: 4,677,100
[45] Date of Patent: Jun. 30, 1987

[54] CEPHALOSPORIN DERIVATIVES

[75] Inventors: Susumu Nakagawa; Ryosuke Ushijima; Fumio Nakano; Koji Yamada, all of Okazaki; Eiichi Mano, Kariya, all of Japan

[73] Assignee: Banyu Pharmaceutical Co., Ltd., Tokyo, Japan

[21] Appl. No.: 813,614

[22] Filed: Dec. 26, 1985

[30] Foreign Application Priority Data

Dec. 27, 1984 [JP] Japan ................. 59-273591
Aug. 6, 1985 [JP] Japan ................. 60-171839

[51] Int. Cl.$^4$ ................. A61K 31/545; C07D 501/46
[52] U.S. Cl. ................. 514/202; 540/222
[58] Field of Search ................. 544/22; 514/202

[56] References Cited

U.S. PATENT DOCUMENTS

| | | | |
|---|---|---|---|
| 4,098,888 | 7/1978 | Ochiai et al. | 540/222 |
| 4,152,432 | 5/1979 | Heymes et al. | 540/227 |
| 4,160,830 | 7/1979 | Morimoto et al. | 514/202 |
| 4,168,309 | 9/1979 | Ayres | 540/222 |
| 4,200,575 | 4/1980 | Numata et al. | 540/222 |
| 4,260,747 | 4/1981 | Heymes et al. | 540/227 |
| 4,264,595 | 4/1981 | Numata et al. | 540/222 |
| 4,379,787 | 4/1983 | Lunn et al. | 540/222 |
| 4,382,931 | 5/1983 | Lunn et al. | 540/222 |
| 4,382,932 | 5/1983 | Lunn et al. | 540/222 |
| 4,396,619 | 8/1983 | Lunn et al. | 540/222 |
| 4,396,620 | 8/1983 | Lunn | 540/222 |
| 4,406,899 | 9/1983 | Aburaki et al. | 544/22 |
| 4,416,879 | 11/1983 | Takaya et al. | 540/222 |
| 4,459,929 | 7/1984 | Kamachi et al. | 544/22 |
| 4,525,473 | 6/1985 | Aburaki et al. | 514/202 |

FOREIGN PATENT DOCUMENTS

| | | |
|---|---|---|
| 111935 | 6/1984 | European Pat. Off. . |
| 0121244 | 10/1984 | European Pat. Off. ............ 544/22 |
| 137440 | 4/1985 | European Pat. Off. . |
| 137442 | 4/1985 | European Pat. Off. . |
| 1399086 | 6/1975 | United Kingdom . |

OTHER PUBLICATIONS

Alfred Burger, Ed., "Medicinal Chemistry", 2nd Ed., Interscience Publishers, Inc, New York (1960), pp. 42–43.
Organic Synthesis, Coll., vol. 5, pp. 406 and 1064.
J. Am. Chem. Soc., vol. 72, 2989.
Journal of Antibiotics, vol. 39 (2), pp. 230–241, Feb. 1986.

Primary Examiner—Robert Gerstl
Assistant Examiner—Barbara Cassatt
Attorney, Agent, or Firm—Oblon, Fisher, Spivak, McClelland & Maier

[57] ABSTRACT

A compound having the formula:

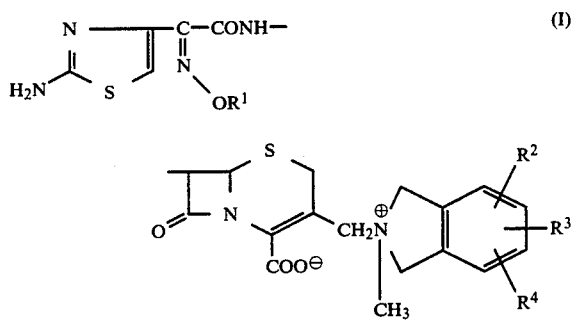

wherein $R^1$ is a straight chain, branched chain or cyclic lower alkyl group which may be substituted by a carboxyl group, and each of $R^2$ and $R^3$ which may be the same or different, is a hydrogen atom, a hydroxyl group, a methoxy group or an acetoxy group, and $R^4$ is a hydroxyl group, a methoxy group or an acetoxy group; or a pharmaceutically acceptable salt, physiologically hydrolyzable ester or solvate thereof.

8 Claims, No Drawings

CEPHALOSPORIN DERIVATIVES

The present invention relates to cephalosporin derivatives, processes for their preparation and antibacterial agents containing them as active ingredients.

Since β-lactam antibiotics exhibit selective toxicity only against bacteria and present no substantial effects against animal cells, they have performed important roles as antibiotics with no substantial side effects in the prevention or treatment of diseases caused by the infection of bacteria.

Particularly, cephalosporin derivatives are generally stable against penicillinase and have a broad antibacterial spectrum, and thus they are frequently employed for the prevention and treatment of diseases caused by the infection of bacteria.

As published technical disclosures which describe cephalosporin derivatives having a quaternary ammonium salt substructure, there may be mentioned Japanese Unexamined Patent Publication Nos. 53690/1978, 59196/1980, 174387/1983 and 198490/1983.

At present, cephalosporin derivatives referred to as the third generation, such as Cefotaxime [Antimicrobial Agents and Chemotherapy, 14 749 (1978)], exhibit excellent antibacterial activities against Gram-positive bacteria and Gram-negative bacteria, particularly against Enterobacteriacae.

Ceftazidime [Antimicrobial Agents and Chemotherapy, 17 876 (1980)] is the most excellent cephalosporin derivative against Gram-negative bacteria including Pseudomonas aeruginosa and Acinetobacter, among various cephalosporin derivatives which have been ever known.

However, the existing third generation cephalosporins in general have relatively poor antibacterial activities against resistant Staphylococcus having various resistant mechanisms, or against glucose non-fermentative Gram-negative rods such as resistant Pseudomonas aeruginosa, and Acinetobacter calcoaceticus.

Further, the above-mentioned Ceftazidime is not necessarily satisfactory because of existence of resistant bacteria.

Accordingly, a novel cephalosporin derivative having a more potent and broader antibacterial spectrum is desired for the curing of obstinate infectious diseases caused by such bacteria.

As mentioned above, cephalosporin derivatives of the so-called third generation, such as Cefotaxime, exhibit relatively poor antibacterial activities against Gram-positive bacteria, and excellent activities against Gram-negative bacteria, particularly against Enterobacteriacae, but few of them exhibit satisfactory antibacterial activities against Pseudomonads and Acinetobacters.

Accordingly, a more powerful and effective medicine is desired for the treatment of serious diseases caused by the infection of these bacteria or by the mixed infection of these bacteria and other bacteria.

The present inventors have conducted extensive reserches on novel cephem compounds having a 2-methyl-substituted isoindolinium methyl group at the 3-position of the cephem, and have found that compounds in which a hydroxyl group or an acetoxy group is incorporated in an isoindoline ring exhibit remarkably strong antibacterial activities against Gram-negative bacteria, particularly against glucose non-fermentative Gram-negative rods such as Pseudomonas aeruginosa, Pseudomonas cepacia and the like, as compared with compounds in which an isoindoline ring is unsubstituted. The present invention has been accomplished on the basis of this discovery.

The present invention provides a compound having the formula:

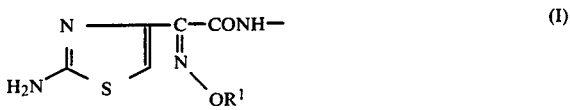

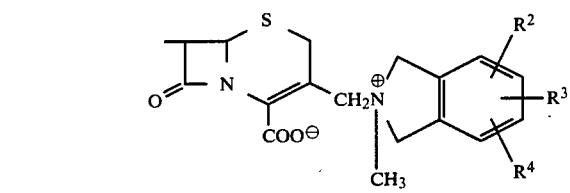

wherein $R^1$ is a straight chain, branched chain or cyclic lower alkyl group which may be substituted by a carboxyl group, and each of $R^2$ and $R^3$ which may be the same or different, is a hydrogen atom, a hydroxyl group, a methoxy group or an acetoxy group, and $R^4$ is a hydroxyl group, a methoxy group or an acetoxy group; or a pharmaceutically acceptable salt, physiologically hydrolyzable ester or solvate thereof.

The compounds of the present invention exhibit superior antibacterial activities against sensitive strains of these bacteria as compared with Ceftazidime, and also exhibit excellent antibacterial activities against Ceftazidime-resistant Pseudomonas and Acinetobactor.

Among such compounds, compounds having a 2-(2-aminothiazol-4-yl)-2-substituted oxyiminoacetyl group as a side chain at the 7-position and a 2-methyl-5,6-disubstituted isoindolinium methyl are particularly excellent in antibacterial activities.

Generally, the substitution of an oxyimino group may take a E-form or a Z-form in the geometrical isomerism. However, the substitution of the oxyimino group in the acylamino moiety at the 7-position of the compound of the formula I has a Z-form.

As the straight chain, branched chain or cyclic lower alkyl group which may be substituted by a carboxyl group for $R^1$ in the formula I, there may be mentioned, for instance, methyl, ethyl, n-propyl, isopropyl, n-butyl, carboxymethyl, 1-carboxy-1-methylethyl, cyclopropyl, cyclobutyl, cyclop-ntyl, cyclohexyl, 1-carboxy-1-cyclopropyl, 1-carboxy-1-cyclobutyl, 1-carboxy-1-cyclopentyl or 1-carboxy-1-cyclohexyl.

As the substituted isoindoline ring of the 2-methyl-substituted isoindolinium methyl at the 3-position of the cephem, there may be mentioned, for instance, 5-hydroxyisoindoline, 5-acetoxyisoindoline, 5-methoxyisoindoline, 4,5-dihydroxyisoindoline, 5,6-dihydroxyisoindoline, 4,5-diacetoxyisoindoline, 5,6-diacetoxyisoindoline, 4,5-dimethoxyisoindoline, 5,6-dimethoxyisoindoline, 4,5-dihydroxy-6-methoxyisoindoline, 4,5-dihydroxy-7-methoxyisoindoline, 5,6-dihydroxy-4-methoxyisoindoline, 4,5-diacetoxy-7-methoxyisoindoline, 5,6-diacetoxy-4-methoxyisoindoline, 4,5-diacetoxy-6-methoxyisoindoline, 4,5,6-trihydroxyisoindoline, 4,5,7-trihydroxyisoindoline, 4,5,6-triacetoxyisoindoline, 4,5,7-triacetoxyisoindoline, 4,5,6-trimethoxyisoindoline or 4,5,7-trimethoxyisoindoline.

The compound of the formula I can be produced by a process (Process A) which comprises reacting a compound having the formula:

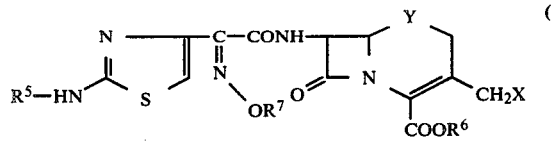
(II)

wherein $R^5$ is a hydrogen atom or an amino protecting group, $R^6$ is a hydrogen atom or a carboxyl-protecting group, $R^7$ is a straight chain, branched chain or cyclic lower alkyl group which may be substituted by a protected carboxyl group, X is a halogen atom or a leaving group, and Y is S or SO, or a salt thereof, with an amine having the formula:

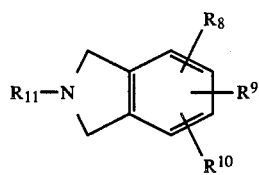
(III)

wherein each of $R^8$ and $R^9$ which may be the same or different, is a hydrogen atom, a protected or unprotected hydroxyl group, a methoxy group or an acetoxy group, and $R^{10}$ is a protected or unprotected hydroxyl group, a methoxy group or an acetoxy group, and $R^{11}$ is a hydrogen atom or a methyl group, to form a compound having the formula:

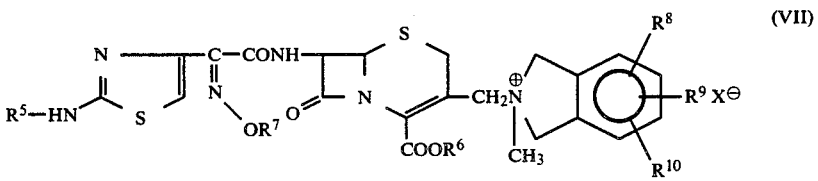
(IV)

wherein $R^5$, $R^6$, $R^7$, $R^8$, $R^9$, $R^{10}$, $R^{11}$ and Y are as defined above, and $X^\ominus$ is an anion, and optionally methylating and/or reducing the compound of the formula IV, followed by the removal of the protecting groups; or a process (Process B) which comprises acylating a compound having the formula:

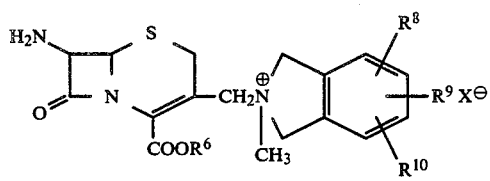
(V)

wherein $R^{6\,1}$ is a hydrogen atom or a carboxyl-protecting group, each of $R^8$ and $R^9$ which may be the same or different, is a hydrogen atom, a protected or unprotected hydroxyl group, a methoxy group or an acetoxy group, and $R^{10}$ is a protected or unprotected hydroxyl group, a methoxy group or an acetoxy goup, and $X^\ominus$ is an anion, or a salt or silyl compound thereof, with a reactive derivative of a carboxylic acid having the formula:

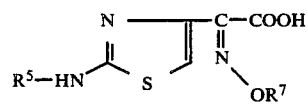
(VI)

wherein $R^5$ is a hydrogen atom or an amino-protecting group, $R^7$ is a straight chain, branched chain or cyclic lower alkyl group which may be substituted by a protected carboxyl group, to form a compound having the formula:

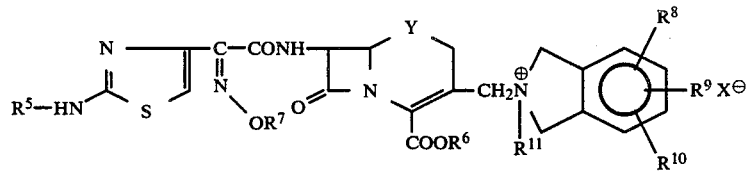
(VII)

wherein $R^5$, $R^6$, $R^7$, $R^8$, $R^9$, $R^{10}$ and $X^\ominus$ are as defined above, followed by the removal of the protecting groups.

As the amino-protecting group for $R^5$ in the compound of the formula II or the formula VI, there may be mentioned, for instance, trityl, formyl, chloroacetyl, trifluoroacetyl, t-butoxycarbonyl, trimethylsilyl or t-butyldimethylsilyl. Particularly preferred is trityl which can readily be removed by acid treatment.

As the carboxyl-protecting group for $R^6$ and $R^7$, there may be mentioned, for instance, the following protecting groups: a lower alkyl group such as t-butyl; a haloalkyl group such as 2,2,2-trichloroethyl; an alkanoyloxyalkyl group such as acetoxymethyl, propionyloxymethyl, pivaloyloxymethyl, 2-acetoxyethyl, 2-propionyloxymethyl or 1-(ethoxycarbonyloxy)-1-ethyl; a 1-phthalidyl group; an alkanesulfonylalkyl group such as mesylmethyl or 2-mesylethyl; an aralkyl group such as benzyl, 4-methoxybenzyl, 4-nitrobenzyl, phenetyl, trityl, benzhydryl, bis(4-methoxyphenyl)-methyl or 3,4-dimethoxybenzyl; 5-substituted-2-oxo-1,3-dioxol-4-yl-methyl group such as 5-methyl-2-oxo-1,3-dioxol-4-yl-methyl group; and an alkylsilyl group such as trimethylsilyl or t-butyldimethylsilyl. Particularly preferred is benzhydryl or t-butyl which can readily be removed by acid treatment.

For the substituent X in the compound of the formula II, the halogen atom may be chlorine, bromine or iodine, and the leaving group may be, for instance, acetoxy, mesyl, trifluoroacetoxy, trifluoroacetyl, methanesulfonyloxy, trifluoromethanesulfonyloxy, phenylsulfonyloxy or p-tolylsulfonyloxy. Particularly preferred is bromine or iodine.

As the reactive derivative of a carboxylic acid of the formula VI, there may be employed, for instance, an acid halide, a mixed acid anhydride or an active ester. The acid halide of the carboxylic acid of the formula VI is obtainable by reacting the carboxylic acid of the formula VI with a halogenating agent. This acid halide-forming reaction may be conducted in an inert solvent such as methylene chloride, chloroform, dichloroethane, benzene or toluene, or a mixture thereof. As the halogenating agent, there may be employed, for instance, thionyl chloride, phosphorus trichloride, phosphorus oxychloride, phosphorus pentachloride, phosphorus tribromide, oxalyl chloride or phosgene. The halogenating agent is used in an amount of from 1 to 10 mols, preferably from 1 to 1.5 mols, per mol of the carboxylic acid of the formula VI. The reaction temperature is usually from −40° to 100° C., preferably from −20° to +20° C. The reaction time is from 10 to 60 minutes.

The mixed acid anhydride of the carboxylic acid of the formula VI can be obtained by reacting the carboxylic acid of the formual VI with an alkyl chlorocarbonate or an aliphatic carboxylic acid chloride. The reaction is conducted in an inert solvent such as acetone, dioxane, acetonitrile, tetrahydrofuran, methylene chloride, chloroform, benzene, ethyl acetate or dimethylformamide, or a mixture thereof. The reaction is preferably conducted in the presence of a tertiary amine such as triethylamine or N-methylmorpholine. The reaction temperature is usually from −30° to 20° C., preferably from −15° to 0° C. The reaction time is from 10 to 30 minutes.

The active ester of the carboxylic acid of the formula VI is obtainable by reacting the carboxylic acid of the formula VI with preferably from 1 to 1.2 mols of an N-hydroxy compound or a phenol compound. The reaction is conducted in an inert solvent such as acetone, dioxane, acetonitrile, tetrahydrofuran, methylene chloride, chloroform, ethyl acetate or dimethylformamide, or a mixture thereof. As the N-hydroxy compound, there may be mentioned, for instance, N-hydroxysuccinimide, N-hydroxyphthalimide or 1-hydroxybenzotriazole, and as the phenol compound, there may be employed, for instance, 4-nitrophenol, 2,4-dinitrophenol, trichlorophenol or pentachlorophenol. This reaciton is preferably conducted in the presence of a condensation agent such as from 1 to 1.2 mols of N,N'-dicyclohexylcarbodiimide. The reaction temperature is usually from −30° to 40° C., preferably from −10° to 25° C. The reaction time is usually from 30 to 120 minutes.

The compound of the formula II wherein Y is S, may be prepared by acylating a compound having the formula:

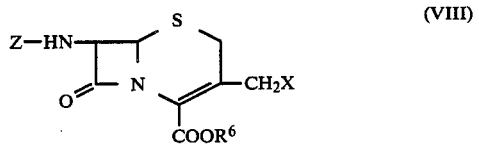

wherein $R^6$ and X are as defined above, and Z is a hydrogen atom or an acyl group, with an reactive derivative of a carboxylic acid of the formula VI. On the other hand, the compound of the formula II wherein Y is SO, may be obtained by oxidizing the compound of the formula II wherein Y is S. The compound of the formula II wherein X is iodine, is preferably prepared by reacting a compound of the formula II wherein X is chlorine, with sodium iodide.

The compound of the formula V is obtainable by reacting a compound of the formula VIII wherein Z is an acyl group, with an amine of the formula III wherein $R^{11}$ is a methyl group, followed by deacylation.

The compound of the formula VIII can be readily prepared from a compound having the formula:

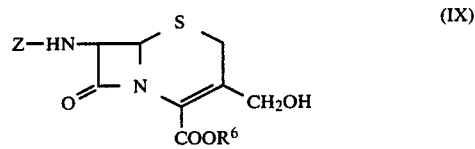

wherein $R^6$ and Z are as defined above.

For the preparation of the compound of the formula I according to Process A, firstly, the compound of the formula II is reacted in a solvent with a free amine of the formula III or an amine salt thereof. When a hydrochloride, hydrobromide, sulfate or acetate is used as the amine salt, the reaction is usually conducted in the presence of a tertiary amine such as triethylamine in an amount sufficient for neutralization. As the solvent, there may be employed a non-aqueous organic solvent such as methylenechloride, chloroform, ether, ethyl acetate, butyl acetate, tetrahydrofuran, acetonitrile, dimethylformamide or dimethylsulfoxide, or a mixture thereof. The amine of the formula III may be silylated in the above-mentioned solvent with a silylating agent such as N,O-bistrimethylsilylacetamide. The amine of the formula III is used usually in an amount of from 1 to 2 mols per mol of the compound of the formula II. The reaction temperature is usually from 0° to 35° C., and the reaction usually completes in from 0.5 to 5 hours.

In the case where a secondary amine of the formula III wherein $R^{11}$ is a hydrogen atom is employed, the resulting product of the formula IV may be reacted, without being isolated, i.e. as in the reaction solution, or after being separated and purified, with methyl iodide to form an ammonium compound of the formula IV. This methylation reaction may be conducted in a solvent. As such a solvent, the above-mentioned non-aqueous organic solvent is preferably employed. When the methylation reaction is conducted in the above-mentioned non-aqueous organic solvent, methyl iodide is used usually in an amount of from 1 to 30 mols, preferably from 3 to 15 mols per mol of the resulting product of the formula IV, and the reaction temperature is usually from −30° to 35° C. The reaction is usually completed in a few hours to a few days. It is also possible to obtain the ammonium compound of the formula IV by reacting the product of the formula IV in the absence of a solvent with excess methyl iodide at a temperature of from 10° to 35° C. for from 5 to 20 hours.

In the case where a compound of the formula II wherein Y is SO is used, the ammonium compound of the formula IV is reduced by a conventional method, for instance, by a method disclosed in e.g. Journal of Organic Chemistry, Vol. 35, 2430 (1970), Synthesis, 58 (1979) or Journal of Chemical Research, 341 (1979). For instance, the product of the formula IV is dissolved in an inert organic solvent such as acetone, methylene chloride, chloroform, tetrahydrofuran or ethyl acetate, and potassium iodide or sodium iodide is added thereto, and acetyl chloride is then dropwise added at a temperature of −40° to 0° C. The reaciton is conducted at a temperature of from −20° to −10° C. for from 1 to 2 hours to accomplish the reduction. The iodide is used in an amount of from 3.5 to 10 mols per mol of the product of the formula IV, and the acetyl chloride is used in an amount of from 1.5 to 5 mols. The compound of the formula I is obtainable by removing the protective groups from the compound thus obtained.

The method for removing the protective groups may optionally be selected from the conventional methods, depending upon the type of the protecting groups. It is preferred to employ a method of using an acid. As such an acid, there may be mentioned an inorganic or organic acid such as formic acid, trifluoroacetic acid, benzene sulfornic acid, p-toluene sulfonic acid or hydrochloric acid. Trifluoroacetic acid is preferred. In the case where trifluoroacetic acid is employed, the reaction may be accelerated by an addition of anisole. Further, this reaction may be conducted in an inert solvent, for instance, an organic solvent such as methylene chloride, ethylene chloride or benzene, or a solvent mixture thereof, preferably in methylene chloride. The reaction temperature is not particularly limited, and may optionally be selected depending upon the chemical nature of the starting compounds and the reaction products, or the type of the protecting groups or the manner of their removal. The reaction is preferably conducted under cooling or under a mild condition of moderate warming.

For the production of the compound of the formula I accoridng to Process B, firstly the compound of the formula V is reacted with a reactive derivative of a carboxylic acid of the formula VI in a solvent. The reaction is conducted in an inert solvent such as water, acetone, dioxane, acetonitrile, tetrahydrofuran, methylene chloride, chlcroform, benzene, ethyl acetate or dimethylformamide, or a mixture thereof. The reactive derivative of a carboxylic acid of the formula VI is used usually in an amount of from 1 to 1.5 mols per mol of the compound of the formula V. The reaction temperature is usually from −40° to 40° C., preferably from −20° to 30° C. In the case where an acid chloride or a mixed acid anhydride of the carboxylic acid of the formula VI is employed, the reaction is preferably conducted in the presence of an alkali metal carbonate or an organic amine such as trimethylamine, triethylamine or N-methylmorpholine.

After the completion of the reaction, the product of the formula VII is separated, and the protective groups are removed in the same manner as in Process A to obtain a compound of the formula I.

The compound of the formula I may be converted into a salt, physiologically hydrolyzable ester or solvate.

As the salt of the compound of the formula I, there may be mentioned a pharmaceutically acceptable common salt, for instance, a salt of an alkali metal such as sodium or potassium, an alkaline earth metal such as calcium or magnesium, an organic amine such as N,N′-dibenzylethylenediamine or procaine, an inorganic acid such as hydrochloric acid, sulfuric acid, nitric acid, perchloric acid or hydrobromic acid, an organic acid such as acetic acid, lactic acid, propionic acid, maleic acid, fumaric acid, malic acid tartaric acid or citric acid, an organic sulfonic acid such as methanesulfonic acid, isethionic acid or p-toluenesulfonic acid, or an amino acid such as asparaginic acid or glutamic acid. As the physiologically hydrolyzable ester, there may be preferably employed an acetoxyalkyl ester such as acetoxymethylester or pivaloyloxymethyl, an alkoxycarbonyloxyalkyl ester such as 1-(ethoxycarbonyloxy)-1-ethyl, 1-phthalizyl ester or a 5-substituted-2-oxo-1,3-dioxol-4-ylmethyl ester such as 5-methyl-2-oxo-1,3-dioxol-4-ylmethyl.

The minimum inhibitory concentrations (MIC: μg/ml) of the compounds of the present invention against various microorganisms were measured by an agar plate dilution method (inoculum size: $10^6$ CFU/ml) by using Sensitivity Disk Agar (Nissui) in comparison with Cefotaxime and Ceftazidime as comparative compounds. The results are shown in Table 1.

TABLE 1

| | Minimum Inhibitory Concentration (μg/ml; $10^6$ CFU/ml) | | | | | | | | |
|---|---|---|---|---|---|---|---|---|---|
| Test microorganism | Compound of Ex. 1-F | Compound of Ex. 2-D | Compound of Ex. 3-D | Compound of Ex. 4-D | Compound of Ex. 5-D | Compound of Ex. 7-E | Cefotaxime | Ceftazidime | Compound of Reference Ex. |
| 1. S. aureus NIHJJC-1 | 0.39 | 0.39 | 6.25 | 6.25 | 3.12 | 25 | 0.78 | 3.12 | 0.39 |
| 2. S. aureus JS-1 | 6.25 | 6.25 | 25 | 25 | 12.5 | >25 | 6.25 | >25 | 3.12 |
| 3. E. coli NIHJJC-2 | ≦0.05 | ≦0.05 | ≦0.05 | ≦0.05 | ≦0.05 | ≦0.05 | ≦0.05 | 0.1 | ≦0.05 |
| 4. E. coli CSH2 | ≦0.05 | ≦0.05 | 0.2 | 0.2 | 0.1 | ≦0.05 | ≦0.05 | 0.1 | ≦0.05 |
| 5. K. pneumoniae No. 42 | 0.2 | 0.2 | 0.2 | 0.2 | 0.1 | ≦0.05 | ≦0.05 | 0.39 | 0.20 |
| 6. P. vulgaris No. 33 | 0.1 | 0.1 | 0.2 | 0.78 | 0.2 | 0.2 | ≦0.05 | ≦0.05 | 0.20 |
| 7. P. mirabilis JY10 | 0.39 | 0.39 | 0.39 | 0.39 | 0.2 | 0.1 | ≦0.05 | ≦0.05 | 0.39 |
| 8. S. marcescens No. 16-2 | 12.5 | 6.25 | 6.25 | 6.25 | 3.12 | 0.39 | 6.25 | 1.56 | 12.5 |
| 9. E. cloaceae Nek 39 | 0.78 | 0.78 | ≦0.05 | ≦0.05 | ≦0.05 | ≦0.05 | 0.78 | 0.78 | 0.78 |
| 10. E. coli CSH | 0.78 | 0.39 | 1.56 | 1.56 | 0.2 | 0.1 | 0.1 | 0.1 | 0.39 |
| 11. C. freundii No. 7 | 1.56 | 1.56 | 6.25 | 6.25 | 6.25 | 0.78 | 0.39 | 1.56 | 1.56 |
| 12. P. aeruginosa AK109 | 3.12 | 3.12 | 0.2 | 0.1 | 0.1 | ≦0.05 | 6.25 | 0.39 | 3.12 |
| 13. P. aeruginosa AKR17 | >25 | >25 | 0.78 | 0.78 | 0.39 | ≦0.05 | >25 | >25 | >25 |
| 14. P. cepacia 23 | 6.25 | 6.25 | 0.39 | 0.2 | 0.1 | ≦0.05 | 3.12 | 0.39 | 12.5 |
| 15. A. calcoaceticus No. 14 | 25 | 25 | 0.2 | 0.2 | 0.2 | 0.1 | 25 | 6.25 | 25 |
| 16. E. coli W3630/Rms212 | 0.2 | 0.2 | ≦0.05 | ≦0.05 | ≦0.05 | ≦0.05 | 0.1 | 0.2 | 0.20 |
| 17. E. coli W3630/Rms213 | 0.78 | 0.78 | 0.78 | 0.78 | 0.2 | ≦0.05 | 0.2 | 0.2 | 0.78 |
| 18. E. coli ML1410/Rte16 | 0.1 | 0.1 | 0.1 | 0.1 | 0.1 | ≦0.05 | ≦0.05 | 0.2 | 0.05 |
| 19. E. coli C/Rms149 | 0.1 | 0.1 | 0.1 | 0.1 | 0.1 | ≦0.05 | ≦0.05 | 0.2 | 0.10 |
| 20. P. vulgaris OB1043 | 0.78 | 0.39 | 3.12 | 3.12 | 0.78 | 0.1 | 0.39 | ≦0.05 | 0.78 |
| 21. P. maltophilia IID 1275 | >25 | >25 | 25 | 25 | 25 | 3.12 | >25 | >25 | >25 |

| Minimum Inhibitory Concentration (μg/ml; $10^6$ CFU/ml) | | | | | |
|---|---|---|---|---|---|
| Compound | Compound | Compound | Compound | Compound | Compound |

TABLE 1-continued

| Test microorganism | of Ex. 8-E | of Ex. 9-C | of Ex. 10-E | of Ex. 11-F | of Ex. 12-C | of Ex. 13-D | Cefotaxime | Cefta-zidime | Compound of Reference Ex. |
|---|---|---|---|---|---|---|---|---|---|
| 1. S. aureus NIHJJC-1 | 12.5 | 6.25 | 25 | 25 | 25 | 3.12 | 0.78 | 3.12 | 0.39 |
| 2. S. aureus JS-1 | >25 | 12.5 | >25 | >25 | >25 | 12.5 | 6.25 | >25 | 3.12 |
| 3. E. coli NIHJJC-2 | ≦0.05 | ≦0.05 | ≦0.05 | ≦0.05 | ≦0.05 | 0.05 | ≦0.05 | 0.10 | ≦0.05 |
| 4. E. coli CSH2 | ≦0.05 | ≦0.05 | ≦0.05 | ≦0.05 | 0.10 | 0.10 | ≦0.05 | 0.10 | ≦0.05 |
| 5. K. pneumoniae No. 42 | ≦0.05 | 0.10 | 0.10 | ≦0.05 | 0.10 | 0.10 | ≦0.05 | 0.39 | 0.20 |
| 6. P. vulgaris No. 33 | 0.10 | 0.10 | ≦0.05 | ≦0.05 | 0.10 | 0.10 | ≦0.05 | ≦0.05 | 0.20 |
| 7. P. mirabilis JY10 | 0.20 | 0.10 | ≦0.05 | ≦0.05 | ≦0.05 | 0.05 | ≦0.05 | ≦0.05 | 0.39 |
| 8. S. marcescens No. 16-2 | 0.78 | 0.78 | 0.39 | 0.20 | 0.39 | 0.78 | 6.25 | 1.56 | 12.5 |
| 9. E. cloaceae Nek 39 | ≦0.05 | ≦0.05 | ≦0.05 | ≦0.05 | 0.10 | 0.05 | 0.78 | 0.78 | 0.78 |
| 10. E. coli CSH | 0.1 | 0.10 | ≦0.05 | ≦0.05 | 0.10 | 0.10 | 0.10 | 0.10 | 0.39 |
| 11. C. freundii No. 7 | 0.78 | 3.12 | 1.56 | 0.78 | 1.56 | 1.56 | 0.39 | 1.56 | 1.56 |
| 12. P. aeruginosa AK109 | ≦0.05 | ≦0.05 | ≦0.05 | ≦0.05 | ≦0.05 | 0.05 | 6.25 | 0.39 | 3.12 |
| 13. P. aeruginosa AKR17 | 0.2 | 0.39 | 0.10 | 0.10 | 0.10 | 0.39 | >25 | >25 | >25 |
| 14. P. cepacia 23 | ≦0.05 | ≦0.05 | ≦0.05 | ≦0.05 | ≦0.05 | 0.10 | 3.12 | 0.39 | 12.5 |
| 15. A. calcoaceticus No. 14 | ≦0.05 | 0.20 | 0.20 | 0.10 | 0.20 | 0.78 | 25 | 6.25 | 25 |
| 16. E. coli W3630/Rms212 | ≦0.05 | ≦0.05 | ≦0.05 | ≦0.05 | ≦0.05 | 0.025 | 0.10 | 0.20 | 0.20 |
| 17. E. coli W3630/Rms213 | ≦0.05 | ≦0.05 | ≦0.05 | ≦0.05 | ≦0.05 | 0.05 | 0.20 | 0.20 | 0.78 |
| 18. E. coli ML1410/Rte16 | ≦0.05 | ≦0.05 | ≦0.05 | ≦0.05 | ≦0.05 | 0.05 | ≦0.05 | 0.20 | 0.05 |
| 19. E. coli C/Rms149 | ≦0.05 | ≦0.05 | ≦0.05 | ≦0.05 | ≦0.05 | 0.05 | ≦0.05 | 0.20 | 0.10 |
| 20. P. vulgaris OB1043 | 0.2 | 0.20 | ≦0.05 | ≦0.05 | ≦0.05 | 0.20 | 0.39 | ≦0.05 | 0.78 |
| 21. P. maltophilia IID 1275 | 6.25 | 3.12 | 3.12 | 1.56 | 6.25 | 12.5 | >25 | >25 | >25 |

It is evident from the above results that the compounds of the formula I in which the isoindoline ring has two substituents exhibit excellent antibacterial activities against Gram-negative bacteria, particularly against glucose non-fermentative Gram-negative rods, for instance, Pseudomonas aeruginosa, Pseudomonas cepacia, Pseudomonas maltophilia and Acinetobacter calcoaceticus. These compounds are particularly superior in that they exhibit strong antibacterial activities also against Pseudomonas aeruginosa AKR-17 and Pseudomonas maltophilia IID 1275 resistant to all B-lactam antibiotics.

When hydroxyl groups or acetoxy groups are introduced at the 5 and 6-positions of the isoindoline ring of the compounds, their antibacterial activities against general Gram-negative bacteria, particularly against Pseudomonas and Acinetobacter remarkably increase.

For instance, the compounds of Examples 3D, 4D, 5D, 7E, 8E, 9C, 10E, 11F, 12C and 13D exhibited antibacterial activities against Pseudomonas aeruginosa AK109 at least 16 times as strong as that of the compound (Reference Example) having a methoxyimino group in the acyl side chain and no substituent in the isoindoline ring, respectively. Against Pseudomonas aeruginosa AKR-17 resistant to all cephalosporins including Ceftazidime, the compounds of Examples 3D, 4D, 5D, 7E, 8E, 9C, 10E, 11F, 12C and 13D exhibited antibacterial activities at least 32 times as strong as that of the unsubstituted compound (Reference Example), respectively. Against Pseudomonas cepacia 23, the compounds of Examples 3D, 4D, 5D, 7E, 8E, 9C, 10E, 11F, 12C and 13D exhibited antibacterial activities at least 32 times as strong as that of the compound of Reference Example, respectively. Against Acinetobacter calcoaceticus, the compounds of Examples 3D, 4D, 5D, 7E, 8E, 9C, 10E, 11F, 12C and 13D exhibited antibacterial activities at least 32 times as strong as that of the compound of Reference Example, respectively. Further, against Pseudomonas maltophilia resistant to all cephalosporins, the compounds of Examples 7E, 8E, 9C, 10E, 11F, 12C and 13D exhibited at least twice as strong as that of the compound of Reference Example, respectively.

The test results of a compound of the present invention for the treatment of infectious diseases of mice caused by the following bacteria are given below by $ED_{50}$(mg/kg), as compared with the results of Ceftazidime.

| Infectious bacteria | Compound of Example 4D | Ceftazidime |
|---|---|---|
| S. aureus Smith | 6.2 | 11 |
| E. coli Juhl | 0.12 | 0.33 |
| P. aeruginosa D15 | 14 | 38 |

The compound of Example 4D exhibited efficacy about twice as high as that of Ceftazidime in the treatment of experimental infections of mice caused by S. aureus Smith, E. coli Juhl and P. aeruginosa D15, as compared with Ceftazidime.

The compounds of the present invention exhibit strong antibacterial activities against sensitive and resistant Gram-positive bacteria and Gram-negative bacteria, particularly against Pseudomonas aeruginosa, Pseudomonas cepacia and Acinetobacter calcoaceticus.

Acordingly, the present invention is useful also as an antibacterial agent comprising an antibacterially effective amount of a compound of the formula I or a pharmaceutically acceptable salt, physiologically hydrolyzable ester or solvate thereof, and a pharmaceutically acceptable carrier.

The compounds of the present invention may be mixed with a carrier of solid or liquid excipient, and may be used in the form of a pharmaceutical formulation suitable for oral administration, parenteral administration or external administration. As the pharmaceutical formulations, there may be mentioned liquid formulations such as injection solutions, syrups or emulsions, solid formulations such as tablets, capsules and granules, and formulations for external application such as ointments and suppositories.

The above-mentioned formulations may contain commonly used additives such as assisting agents, stabilizers, wetting agents or emulsifying agents. For instance, injection solutions may contain a solubilizing liquid for injection such as distilled water, a physiological sodium chloride solution or a Ringer solution and a stabilizer such as methyl p-hydroxybenzoate or propyl p-hydroxybenzoate. Likewise, liquid agents such as syrups and emulsions may contain an emulsifying agents such as gum arabic, gelatin or lecithin and a surfactant such as Tween or Span in addition to sorbitol syrup, methyl cellulose, glucose, sucrose syrup, gelatin, hydroxyethyl cellulose, carboxymethyl cellulose, aluminum stearate gel, an edible oil, almond oil, coconut oil, oil ester, sorbitan monooleate, propylene glycol, glycerin, ethyl alcohol or water. For a solid formulation, lactose, sucrose, corn starch, calcium phosphate, magnesium stearate, talc, silicic acid, gum arabic, gelatin, sorbitol, traganto, polyvinylpyrrolidone, polyethylene glycol or sodium lauryl sulfate, may be employed. As the base material for ointments or suppositories, there may be employed, for instance, cacao butter, glycerides, polyethylene glycols, white vaseline, etc. A surfactant or a absorption accelerating agent may be incorporated, as the case requires.

The compound of the formula I of the present invention may be employed for the prevention and treatment of diseases caused by bacterial infections, such as infectious diseases of the respiratory system, infectiousness of the genito-urinary tract, infectious diseases of pregnant women, suppurative diseases or surgical infectious diseases. The dose may vary depending upon the age and the condition of the patient, and is usually from 1 to 100 mg/kg per day. It is preferred to administer a daily dose of from 5 to 30 mg/kg in 2 to 4 times.

Now, the present invention will be described in further detail with reference to Examples. However, it should be understood that the present invention is by no means restricted to these specific Examples.

EXAMPLE 1

(A) Benzhydryl 7-[(Z)-2-methoxyimino-2-(2-tritylaminothiazol-4-yl)acetamido]-3-chloromethyl-3-cephem-4-carboxylate 1-oxide 2.5 g (2.97 mmol) of benzhydryl 7-[(Z)-2-methoxyimino-2-(2-tritylaminothiazol-4-yl)acetamido]-3-chloromethyl-3-cephem-4-carboxylate was dissolved in 25 ml of benzene, and 640 mg (3.27 mmol) of m-chloroperbenzoic acid was added under cooling with ice. The mixture was stirred at room temperature for 1 hour. The reaction solution was poured into ice water, and extracted with ethyl acetate. The extracted solution was washed with a 5% sodium bisulfite aqueous solution and with a saturated sodium chloride aqueous solution, then dried over anhydrous sodium sulfate and concentrated under reduced pressure, whereby the above identified compound was obtained as a powdery substance.

NMR(CDCl$_3$)δ: 3.25 & 3.70(2H, ABq, J=18 Hz), 4.03(3H, s), 4.13 & 4.70(2H, ABq, J=12 Hz), 4.47(1H, d, J=5 Hz), 6.07(1H, dd, J=5 & 9 Hz), 6.67(1H, s), 6.92(1H, s), 7.3(27H, m)

(B) Benzhydryl 7-[(Z)-2-methoxyimino-2-(2-tritylaminothiazol-4-yl)acetamido]-3-iodomethyl-3-cephem-4-carboxylate 1-oxide The compound obtained in (A) was dissolved in 50 ml of acetone, and 670 mg (4.47 mmol) of sodium iodide was added. The mixture was stirred at room temperature for 30 minutes. The reaction solution was poured into ice water, and extracted with ethyl acetate. The extracted solution was washed with a 5% sodium thiosulfate aqueous solution, with water and with a saturated sodium chloride aqueous solution, then dried over anhydrous sodium sulfate and concentrated under reduced pressure, whereby the above identified compound was obtained as a powdery substance.

IR(KBr): 1790, 1720, 1680, 1510, 1370, 1290, 1230, 1160, 1040 cm$^{-1}$

NMR(CDCl$_3$) δ: 3.4 & 3.68(2H, ABq, J=18 Hz), 4.03(3H, s), 4.48(1H, d, J=5 Hz), 6.0(1H, dd, J=5 & 9 Hz), 6.67(1H, s), 6.95(1H, s), 7.3(27H, m)

(C) Benzhydryl 7-[(Z)-2-methoxyimino-2-(2-tritylaminothiazol-4-yl)acetamido]-3-(5-acetoxyisoindolin-2-yl)methyl-3-cephem-4-carboxylate 1-oxide 2.32 g (2.45 mmol) of the powder obtained in (B) was dissolved in 23 ml of methylene chloride, and 1.2 g (4.65 mmol) of 5-acetoxyisoindoline hydrobromide and 0.8 ml (5.7 mmol) of triethylamine were added thereto. The mixture was stirred at room temperature for 2 hours and concentrated under reduced pressure The residue was subjected to silica gel flush column chromatography (ethyl acetate/n-hexane=3/1) to obtain 2.62 g of the above-identified compound as crude product.

NMR(DMSO-d$_6$) δ: 2.26(3H, s), 3.5-3.9(8H, m), 3.88(3H, s), 5.08(1H, d, J=4 Hz), 5.90(1H, dd, J=4 & 8 Hz), 6.86(1H, s), 6.98(1H, s), 7.03(1H, s), 7.0-7.9(27H, m), 8.74(1H, bs), 8.88(1H, bd, J=8 Hz)

(D) Benzhydryl 7-[(Z)-2-methoxyimino-2-(2-tritylaminothiazol-4-yl)acetamido]-3-(5-acetoxy-2-methyl-2-isoindolinium)-methyl-3-cephem-4-carboxylate 1-oxide iodide 2.6 g of the compound obtained in (C) was dissolved in 20 ml of methyl iodide (treated with alumina), and the solution was left to stand at room temperature for 18 hours. The reaction solution was subjected to slica gel flush column chromatography (2 to 5% methanol-methylene chloride) to obtain 2.34 g of the above-identified compound (yield from the previous step: 79%).

NMR(DMSO-d$_6$) δ: 2.31(3H, s), 3.00(3H, bs), 3.38(2H, bs), 3.90(3H, s), 4.5-5.1(6H, m), 5.15(1H, m), 6.00(1H, dd, J=5 & 7 Hz), 6.85(1H, s), 7.05(1H, s), 7.0-7.8(28H, m), 8.75(1H, bs), 9.11(1H, bd, J=7 Hz)

(E) Benzhydryl 7-[(Z)-2-methoxyimino-2-(2-tritylaminothiazol-4-yl)acetamido]-3-(5-acetoxy-2-methly-2-isoindoliniun)-methyl-3-cephem-4-carboxylate iodide 2.3 g (2.0 mmol) of the compound obtained in (D) was dissolved in 23 ml of acetone, and 1.34 g (8.0 mmol) of potassium iodide was added, and 0.29 ml (4.07 mmol) of acetyl chloride was dropwise added at −10° C. The mixture was stirred for 1 hour. The reaction solution was poured into a 2% sodium metabisulfite-saturated sodium chloride aqueous solution, and extracted with ethyl acetate. Then, the extracted solution was dried over anhydrous sodium sulfate, the solvent was distilled off to obtain 2.68 g (yield: 100%) of the above-identified compound.

NMR(DMSO-d$_6$) δ: 2.30(3H, s), 3.00(3H, bs), 3.88(3H, s), 4.0(2H, m), 4.5-5.1(6H, m),5.35(1H, d), 5.90(1H, m), 6.79(1H, s), 7.01(1H, s), 7.1-7.8(28H, m), 8.85(1H, bs), 9.65(1H, bd, J=8 Hz)

(F) 7-[(Z)-2-aminothiazol-4-yl)-2-methoxyiminoacetamido]3-(5-acetoxy-2-methyl-2-isoindolinium)methyl-3-cephem-4-carboxylate 2.6 g (2.32 mmol) of the compound obtained in (E) was dissolved in 5 ml of methylene chloride and 5 ml of anisole, and 13 ml of trifluoroacetic acid was dropwise added at 0° C. The mixture was stirred for 1 hour. The reaction solution was concentrated under reduced pressure, the residue was dissolved in ethyl acetate and extracted with water. The aqueous layer was subjected to reversed phase chromatography (Waters Pre Pack 500/C-18, 60 ml: 2% tetrahydrofuran-water). The fraction containing the desired product was collected and concentrated under reduced pressure, and then the concentrate was freeze-dried to obtain 579 mg (yield: 48.8%) of the above-identified desired product.

Melting point: 153° C. (decomposed)
IR(KBr): 3400, 1760, 1610 cm$^{-1}$
NMR(CF$_3$COOH) δ: 2.00(3H, s), 3.04(3H, bs), 3.34(2H, bs), 3.78(3H, s), 4.2–4.9(6H, m), 4.92(1H, d, J=5 Hz), 5.5(1H, m), 6.72(1H, s), 6.78(1H, d, J=9 Hz), 6.80(1H, s), 6.95(1H, d, J=9 Hz), 7.0–7.6(2H, m), 8.06(1H, bd)

EXAMPLE 2

(A) Benzhydryl 7-[(Z)-2-methoxyimino-2-(2-tritylaminothiazol-4-yl)acetamido]-3-(5-hydroxyisoindolin-2-yl)-3-cephem-4-carboxylate 1-oxide 2.4 g (2.53 mmol) of the powder obtained in Example 1 (B) was dissolved in 20 ml of N,N-dimethylformamide, and 0.77 g (3.56 mmol) of 5-hydroxyisoindoline hydrobromide and 0.6 ml (4.3 mmol) of triethylamine were added thereto. The mixture was stirred at room temperature for 1 hour. The dimethylformamide was distilled off under reduced pressure. The residue was subjected to silica gel flush column chromatography (ethyl acetate/n-hexane =3/1 to 1/0) to obtain 2.1 g (yield: 87%) of the above-identified compound.

NMR(DMSO-d$_6$) δ: 3.38(2H, bs), 3.40–4.00(6H, m), 3.89(3H, s), 5.08(1H, d, J=4 Hz),5.89(1H, dd, J=4 & 8 Hz), 6.85(1H, s), 7.00(1H, s), 7.0–7.8(28H, m), 8.70(1H, bs), 8.9(1H, bd, J=8 Hz)

(B) Benzhydryl 7-[(Z)-2-methoxyimino-2-(2-tritylaminothiazol-4-yl)acetamido]-3-(5-hydroxy-2-methyl-2-isoindolinium)-methyl-3-cephem-4-carboxylate 1-oxide iodide 2.1 g (2.2 mmol) of the compound obtained in (A) was dissolved in 20 ml (321 mmol) of methyl iodide (treated with alumina), and the mixture was left to stand at room temperature for 12 hours in a dark place. The reaction solution was subjected to silica gel flush column chromatography (2 to 5% methanol-methylene chloride) to obtain 1.9 g (yield: 79%) of the above-identified compound.

NMR(DMSO-d$_6$) δ: 2.92(3H, bs), 3.49(2H, bs), 3.89(3H, s), 4.3–5.2(6H, m), 5.21(1H, d, J=4 Hz), 6.00(1H, dd, J=4 & 8 Hz), 6.86(1H, s), 7.05(1H, s), 7.0–7.8(27H, m), 8.80(1H, bs), 9.16(1H, bd, J=8 Hz)

(C) Benzhydryl 7-[(Z)-2-methoxyimino-2-(2-tritylaminothiazol-4-yl)acetamido]-3-(5-hydroxy-2-methyl-isoindolinium)-methyl-3-cephem-4-carboxylate iodide:

1.9 g (1.73 mmol) of the compound obtained in (B) was dissolved in 19 ml of acetone, and 1.13 g (6.8 mmol) of potassium iodide, and 0.25 ml (3.5 mmol) of acetyl chloride was added at −10° C. The mixture was stirred for 45 minutes. The reaction solution was poured into a 5% sodium metabisulfite-saturated sodium chloride aqueous solution, and extracted with ethyl acetate. Then, the extracted solution was dried over anhydrous sodium sulfate. The solvent was distilled off to obtain 2.18 g of the above-identified compound as crude product The compound thus obtained was employed for the next step without purification.

NMR(DMSO-d$_6$) δ: 2.90(2H, bs), 3.00(3H, bs), 3.90(3H, s), 4.3-5.1(6H, m), 5.42(1H, bd, J=5 Hz), 5.90(1H,dd, J=5 & 8 Hz), 6.80(1H, s), 6.85(2H, bs), 7.02(1H, s), 7.0-7.8(26H, m), 8.9(1H, bs), 9.65(1H, bd, J=8 Hz)

(D) 7-[(Z)-2-(2-aminothiazol-4-yl)-2-methoxyiminoacetamido]-3-(5-hydroxy-2-methyl-2-isoindolinium)methyl-3-cephem-4-carboxylate 2.1 g of the powder obtained in (C) was dissolved in 4 ml of methylene chloride and 4 ml of anisole, and 10 ml of trifluoroacetic acid was added at 0° C. The mixture was stirred for 1 hour. The reaction solution was concentrated under reduced pressure, and the residue was dissolved in ethyl acetate and extracted with water for five times. The aqueous layer was subjected to reversed phase chromatography (Waters Pre Pack 500/C-18: 1 to 2% tetrahydrofuran-water). The fraction containing the desired product was collected and concentrated under reduced pressure, and then the concentrate was freeze-dried to obtain 451 mg of the above-identified desired product (yield from the previous step: 48%).

Melting point: 160° C. (decomposed)
IR(KBr): 3400, 1768, 1610 cm$^{-1}$
NMR(CF$_3$COOH) δ: 3.02(3H, bs), 3.38(2H, bs), 3.85(3H, s), 4.2–4.9(6H, m), 4.98(1H, d, J=5 Hz), 5.5(1H, m), 6.60(1H, s), 6.65(1H, d, J=7 Hz), 6.88(1H, dd, J=7 Hz), 6.96(1H, s), 7.1–7.7(2H, m), 8.08(1H, d, J=8 Hz)

EXAMPLE 3

(A) Benzhydryl 3-(5,6-diacetoxyisoindolin-2-yl) methyl-7-[(Z)-2-methoxyimino-2-(2-tritylaminothiazol-4-yl) acetamido]-3-cephem-4-carboxylate 1-oxide iodide:

2.1 g (2.2 mmol) of the powder obtained in Example 1(B) was dissolved in 40 ml of methylene chloride, and 1.3 g (4.1 mmol) of 5,6-diacetoxyisoindoline hydrobromide and 0.6 ml (4.3 mmol) of triethylamine were added thereto. The mixture was stirred at room temperature for 1 hour. After distillation of methylene chloride, the residue was subjected to silica gel flush column chromatography (1% methanol-methylene chloride) to obtain 1.89 g (yield: 80%) of the powder of the above-identified compound.

NMR(CDCl$_3$) δ: 2.30 (6H, s), 3.65–4.2(8H,m), 4.05(3H, s), 4.56(1H,d,J=4 Hz),6.15(1H,dd,J=4 & 10 Hz), 6.70(1H, s), 6.90(1H, s), 7.0–7.8(27H, m)

(B) Benzhydryl 3-(5,6-diacetoxy-2-methyl-2-isoindolinium) methyl-7-[(Z)-2-methoxyimino-2-(2-tritylaminothiazol-4-yl) acetamido]-3-cephem-4-carboxylate 1-oxide iodide 1.8 g (1.71 mmol) of the powder obtained in (A) was dissolved in 20 ml (321 mmol) of methyl iodide (treated with alumina), and the mixture was left to stand at room temperature for 12 hours in a dark place. The reaction solution was subjected to silica gel flush column chromatography (5% methanol-methylene chloride) to obtain 1.21 g (yield: 59%) of the powder of the above-identified compound.

NMR(DMSO-f$_6$) δ: 2.35(6H, s), 3.10(3H, bs), 3.35(2H, bs), 3.90(3H, s), 4.6-5.2 (6H, m), 5.16(1H, d, J=4 Hz), 6.0(1H, m), 6,85(1H, s), 7.08(1H, s), 7.1-7.8(27H, m), 8.75(1H, bs), 9.12(1H, bs)

(C) Benzhydryl 3-(5,6-diacetoxy-2-methyl-2-isoindolinium)methyl-7-[(Z)-2-methoxyimino-2-(2-tritylaminothiazol-4-yl)acetamido]-3-cephem-4-carboxylate iodide 1.2 g (1.0 mmol) of the powder obtained in (B) was dissolved in 12 ml of acetone, and 0.67 g (4.0 mmol) of potassium iodide was added, and 0.14 ml (1.97 mmol) of acetyl chloride was dropwise added at −10° C. 30 minutes later, 0.67 g (4.0 mmol) of potassium iodide and 0.14 ml (1.97 mmol) of acetyl chloride were further added. The mixutre was stirred for 30 minutes. The reaction solution was poured into a 1% sodium metabisulfite-saturated sodium chloride aqueous solution, and extracted with ethyl acetate. The extracted solution was dried over anhydrous sodium sulfate. The solvent was distilled off to obtain 1.0 g (yield 89%) of the above-identified compound.

NMR(DMSO-d$_6$) δ: 2.40 (6H, s), 3.05 (5H, bs), 3.90(3H, s), 4.5-5.2(6H, m), 5.40(1H, d, J=4 Hz), 5.9(1H, m), 6.82(1H, s), 7.10 (1H, s), 7.0-8.0(27H, m), 8.9(1H, m), 9.65(1H, bd)

(D) 7-[(Z)-2-aminothiazol-4-yl)-2-methoxyiminoacetamido]-3-(5,6-diacetoxy-2-methyl-2-isoindolinium)methyl-3-cephem-4-carboxylate 1.0 g (0.84 mmol) of the powder obtained in (C) was dissolved in 2 ml of methylene chloride and 2 ml of anisole, and 5 ml of trifluoroacetic acid was added at 0° C. The mixture was stirred for 1 hour. The reaction solution was concentrated under reduced pressure, and after an addition of 20 ml of methylene chloride, extracted with water for four times. The aqueous layer was purified by reversed phase chromatography (Waters Pre Pack 500/C-18, 80 ml; 2 to 5% tetrahydrofuran-water). The fraction containing the desired product was collected and concentrated under reduced pressure. Then, the concentrate was freeze-dried to obtain 134 mg (yield: 24.5%) of the above-identified desired compound Melting point: 161° C. (decomposed)
IR(KBr): 3400, 1760, 1605 cm$^{-1}$
NMR(CF$_3$COOH) δ: 2.00(6H, s), 3.07(3H, bs), 3.30(2H, bs), 3.77(3H, s), 4.2-4.8(6H, m), 4.90(1H, d, J=5 Hz), 5.5(1H, m), 6.87(2H, s), 6.90(1H, s), 7.0-7.6(2H, m), 8.08(1H, d, J=7 Hz)

EXAMPLE 4

(A) Benzhydryl 3-(5,6-dihydroxyisoindolin-2-yl) methyl-7-[(Z)-2-methoxyimino-2-(2-tritylaminothiazol-4-yl) acetamido]-3-cephem-4-carboxylate 1-oxide 3.0 g (3.16 mmol) of the powder obtained in Example 1 (B) was dissolved in 15 ml of N,N-dimethylformamide, and 1.2 g (5.17 mmol) of 5,6-dihydroxyisoindoline hydrobromide and 0.8 ml (5.73 mmol) of triethylamine were added thereto. The mixture was stirred at room temperatrue for 90 minutes. The mixture was concentrated under reduced pressure, and the residue was subjected to silica gel flush chromatography (ethyl acetate/n-hexane =3/1 to 1/0) to obtain 2.35 g (yield: 76%) of the above-identified compound.

NMR(CDCl$_3$) δ: 3.4-3.9(8H, m), 4.05(3H, s), 4.68(1H, d, J=5 Hz), 6.12(1H, m), 6.63(2H, s), 6.75(1H, s), 6.98(1H, s), 7.1-7.9(27H, m)

(B) Benzhydryl 3-(5,6-dihydoxy-2-methyl-2-isoindolinium) methyl-7-[(Z)-2-methoxyimino-2-(2-tritylaminothiazol-4-yl) acetamido]-3-cephem-4-carboxylate 1-oxide iodide 2.3 g (2.37 mmol) of the compound obtained in (A) was dissolved in 20 ml (321 mmol) of methyl iodide (treated with alumina). The mixture was left to stand at room temperature for 12 hours in a dark place. The reaction solution was subjected to silica gel flush column chromatography (10% methanol-methylene chloride) to obtain 1.29 g (yield: 49%) of the above-identified compound.

NMR(DMSO-d$_6$) δ: 2.94(3H, bs), 3,48 (2H, bs), 3.90(3H, s), 4.2-5.3(6H, m), 5,30(1H, d, J=5 Hz), 6.05(1H, dd, J=5 & 8 Hz), 6.83(1H, s), 6.90(1H, s), 7.08(1H, s), 6.9-7.9(27H, m), 9.20(1H, bd, J=8 Hz), 9.40(1H, bs)

(C)Benzhydryl 3-(5,6-dihydroxy-2-methyl-2-isoindolinium) methyl-7-[(Z)-2-methoxyimino-2-(2-tritylaminothiazol-4-yl) acetamido]-3-cephem-4-carboxylate iodide 1.29 g (1.16 mmol) of the compound obtained in (B) was dissolved in 13 ml of acetone, and 0.7 g (4.2 mmol) of potassium iodide was added, and 0.15 ml (2.11 mmol) of acetyl chloride was dropwise added at −10° C. The mixture was stirred for 40 minutes. The reaction solution was poured into a 2% sodium metabisulfite-saturated sodium chloride aqueous solution, and then extracted with ethyl acetate and dried over anhydrous sodium sulfate, and the solvent was distilled off. The residue was also treated in the same manner as above to obtain 1.8 g of the above-identified compound. The compound thus obtained was employed for the next step without purification.

NMR(DMSO-d$_6$) δ: 2.88(3H, bs), 2.9(2H, bs), 3.88(3H, s), 4.3-5.1(6H, m), 5.40(1H, d, J=5 Hz), 5.90(1H, m), 6.81(3H, s), 7.03(1H, s), 7.0-7.8(27H, m), 9.00(1H, bs), 9.68(1H, d, J=8 Hz)

(D) 7-[(Z)-2-(2-aminothiazol-4-yl)-2-methoxyiminoacetamido]-3-(5,6-dihydroxy-2-methyl-2-isoindolinium)methyl-3-cephem-4-carboxylate:

The crude compound obtained in (C) was dissolved in 2 ml of methylene chroride and 2 ml of anisole, and 5 ml of trifluoroacetic acid was added at 0° C. The mixture was stirred for 1 hour. The reaction solution was concentrated under reduced pressure. The residue was dissolved in methylene chloride and extracted with water for five times. The aqueous layer was subjected to reversed phase column chromatography (Waters Pre Pack 500/C-18, 200 ml; 0.5% tetrahydrofuran-water). The fraction containing the desired product was collected and concentrated under reduced pressure, and then the concentrate was freeze-dried to obtain 261 mg of the above-identified desired compound (yield from the previous step: 40%).

Melting point: 152° C. (decomposed)
IR(KBr): 3400, 1775, 1670, 1615 cm$^{-1}$
MNR(CF$_3$COOH) δ: 2.98(3H, bs), 3.27(2H, bs), 3.80(3H, s), 4.2-4.8(6H, m), 4.90(1H, d, J=5 Hz), 5.45(1H, dd, J=5 & 8 Hz), 6.50(2H, s), 6.92(1H, s), 7.0-7.7(2H, m), 8.05(1H, d, J=8 Hz)

EXAMPLE 5

(A) Benzhydryl 3-(5,6-dihydroxyisoindolin-2-yl) methyl-7-[(Z)-2-ethoxyimino-2-(2-tritylaminothiazol-4-yl) acetamido]-3-cephem-4-carboxylate 1-oxide 3 g (3.45 mmol) of benzhydryl 3-chloromethyl-7-[(Z)-2-ethoxyimino-2-(2-tritylaminothiazol-4-yl) acetamido]-3-cephem-4-carboxylate 1-oxide was dissolved in 60 ml of acetone, and 1.14 g (7.6 mmol) of sodium iodide was added. The mixture was stirred at room temperature for 15 minutes. The reaction solution was added to a 10% sodium thiosulfate aqueous solution, and then extracted with ethyl acetate, and dried over anhydrous sodium sulfate. Then, the solvent was distilled off. The concentrated residue was dissolved in 15 ml of N,N-dimethylformamide, and 1.2 g (5.17 mmol) of 5,6-dihydroxyisoindoline hydrobromide and 0.7 ml (5.0 mmol) of triethylamine were added thereto. The mixture was stirred at room temperature for 3 hours, the N,N-dimethylformamide was distilled off under reduced pressure, and the residue was subjected to silica gel flush column chromatography (ethly acetate/n-hexane = $\frac{1}{3}$ to 1/0) to obtain 2.33 g (yield: 69%) of the above-identified compound.

NMR(DMSO-$d_6$) δ: 1.25(3H, t, J=6 Hz), 3.3–3.9 (8H, m), 4.03(2H, q, J=6 Hz), 5.09(1H, d, J=4 Hz), 5.92(1H, dd, J=4 & 8 Hz), 6,60(1H, s), 6.85(1H, s), 7.01(2H, s), 7.0–7.8(25H, m), 8.7(1H, bd,), 8.76(,(1H, bs)

(B) Benzhydryl 3-(5,6-dihydroxy-2-methyl-2-isoindolinium) methyl-7-[(Z)-2-ethoxyimino-2-(2-tritylaminothiazol-4-yl)acetamido]-3-cephem-4-carboxylate 1-oxide iodide 2.39 g (2.48 mmol) of the compound obtained in (A) was dissolved in 20 ml (321 mmol) of methyl iodide (treated with alumina). The mixture was left to stand at room temperature for 12 hours in a dark place. The reaction solution was subjected to silica gel flush column chromatography (5% methanol-methylene chloride) to obtain 2.06 g (yield: 75%) of the above-identified compound NMR(DMSO-$d_6$) δ: 1.25(3H, t, J=6 Hz), 2.90(3H, bs), 3.30(2H, bs), 4.13(2H, q, J=6 Hz), 4.1–5.0(6H, m), 5.20(1H, d, J=5 Hz), 6.00(1H, m), 6.75(2H, bs), 6.81(1H, s), 7.01(1H, s), 7.0–7.6(25H, m), 8.75(1H, bs), 9.00(1H, bd, J=8 Hz), 9.3(1H, bs)

(C) Benzhydryl 3-(5,6-dihydroxy-2-methyl-2-isoindolinium) methyl-7-[(Z)-2-ethoxyimino-2-(2-tritylaminothiazol-4-yl)a cetamido]-3-cephem-4-carboxylate iodide 2.06 g (2.1 mmol) of the compound obtained in (B) was dissolved in 20 ml of acetone, and 1.21 g (7.28 mmol) of potassium iodide was added, and 0.26 ml (3.65 mmol) of acetyl chloride was dropwise added at −10° C. The mixture was stirred for 40 minutes. The reaction solution was poured into a 2% sodium metabisulfite-saturated sodium chloride aqueous solution, then extracted with ethyl acetate and dried over anhydrous sodium sulfate, and then the solvent was distilled off. The residue was also treated in the same manner as above to obtain 2.6 g of the above-identified compound. The compound thus obtained was employed for the next step without purification. NMR(DMSO-$d_6$) δ: 1.25(3H, t, J=6 Hz), 2.9(2H, m), 3.00(2H, s), 4.15(2H, q, J=6 Hz), 4.3–5.0(6H, m), 5.40(1H, d, J=5 Hz), 5.92(1H, m), 6.78(2H, bs), 6.90(1H, bs), 7.01(1H, bs), 7.1–7.8(25H, m), 9.0(1H, m), 9.6(1H, m)

(D) 7-[(Z)-2-(2-aminothiazol-4-yl)-2-ethoxyiminoacetamido]-3-(5,6-dihydroxy-2-methyl-2-isoindolinium) methyl-3-cephem-4-carboxylate 2.6 g of the crude compound obtained in (C) was dissolved in 4 ml of methylene chloride and 4 ml of anisole, and 10 ml of trifluorcacetic acid was added at 0° C. The mixture was stirred for one hour The reaction solution was concentrated under reduced pressure, the residue was dissolved in ethyl acetate and extracted with water for five times. The aqueous layer was subjected to reversed phase column chromatography (Waters Pre Pack 500/C-18, 200 ml: tetrahydrofuran-water =0.1 to 5/95). The fraction containing the desired product was collected, concentrated under reduced pressure and then the concentrate was freeze-dried to obtain 460 mg of the above-identified desired compound (yield from the previous step: 43%).

Melting point: 148° C. (decomposed)
IR(KBr): 3400, 1770, 1610, 1340 cm$^{-1}$
NMR(CF$_3$COOH) δ: 1.03(3H, t, J=7Hz), 3.06(3H, bs), 3.36(2H, bs), 4.14(2H, q, J=7 Hz), 4.2–4.9(6H, m), 5.00(1H, d, J=5 Hz), 5.52(1H, m), 6,59(2H, s), 6.99 (1H, s), 8.18(1H, bd, J=8 Hz)

EXAMPLE 6

(A) Benzhydryl 3-(5,6-dihydroxy-2-methyl-2-isoindolinium) methyl-7-[(Z)-2-methoxyimino-2-(2-tritylaminothiazol-4-yl) acetamido]-3-cephem-4-carboxylate 1-oxide iodide To a suspension of 460 mg (3.3 mmol) of 5,6-dihydroxy-2-methylisoindoline and 25 ml of ethyl acetate, 1.6 ml (6.6 mmol) of N,O-bistrimethylsilylacetamide was added, and the mixture was stirred at 50° C. for 1 hour for solubilization. After cooling the solution to room temperature, it was added at a stretch to a solution of 2.84 g (3 mmol) of benzhydryl 3-iodomethyl-7-[(Z)-2-methoxyimino-2-(2-tritylaminothiazol-4-yl)acetamido]-3-cephem-4-carboxylate 1-oxide and 20 ml of ethyl acetate. The mixture was stirred at room temperature for 4 hours, and then 150 ml of chloroform and 30 ml of water were added thereto for extraction. The organic layer was dried over anhydrous sodium sulfate and concentrated. The residue was purified by silica gel flush column chromatography (3 to 5% methanol-methylene chloride) to obtain 1.78 g (yield: 3.3%) of a powder of the above-identified compound. (B) Benzhydryl 3-(5,6-dihydroxy-2-methyl-2-isoindolinium) methyl-7-[(Z)-2-methoxyimino-2-(2-tritylaminothiazol-4-yl) acetamido]-3-cephem-4-carboxylate iodide: 35 ml of acetone was added to 1.78 g (1.6 mmol) of the compound obtained in (A) and 1.33 g (8 mmol) of potassium iodide. Then 0.28 ml (4 mmol) of acetyl chloride was dropwise added thereto at −20° C. The mixture was stirred at a temperature of from −20° to −10° C. for two hours, and then 1.33 g of potassium iodide and 0.28 ml of acethyl chloride were added. The mixture was further stirred at the same temperature for two hours. To the reaction solution, 100 ml of a cooled 10% sodium metabisulfite aqueous solution-saturated sodium chloride aqueous solution (1/1) and 100 ml of methylene chloride were added for extraction. The organic layer was dried over anhydrous sodium sulfate and concentrated under reduced pressure to obtain a powder of the above-identified compound.

(C) 7-[(Z)-2-(2-aminothiazol-4-yl)-2-methoxyiminoacetamido]-3-(5,6-dihydroxy-2-methyl-2-isoindolinium)methyl-3-cephem-4-carboxylate The compound obtained in (B) was dissolved in 18 ml of methylene chloride, and 1.8 ml of anisole was added. Then, the mixture was cooled, and 18 ml of cooled trifluoroacetic acid was added. The mixture was stirred at the same temperature for five hours, and then the solvent was distilled off under reduced pressure. To the residual solution, 20 ml of ethyl acetate was added, and the mixture was concentrated under reduced pressure The operation was repeated twice. Then 40 ml of diethyl ether was added, and insoluble matters were collected by filtration. The insoluble matters were suspended in 200 ml of water by stirring After separation of the insoluble matters by filtration, the aqueous layer was purified by reversed phase chromatography (Waters Pre Pack 500/C-18, 100 ml; 300 ml of water and 1 l of 1% tetrahydrofuran aqueous solution), and after removal of the organic solvent under reduced pressure, freeze-dried to obtain 330 mg of the above-identified desired compound.

The desired compound exhibited the same IR and NMR as the compound obtained in Example 4(D).

EXAMPLE 7

(A) Benzhydryl 7-[(Z)-2-(1-tert-butoxycarbonyl-1-methylethoxyimino)-2-(2-tritylaminothiazol-4-yl) acetamido]-3-chloromethyl-3-cephem-4-carboxylate 1-oxide 10 g (10.3 mmol) of benzhydryl 7-[(Z)-2-(1-tert-butoxycarbonyl-1-methylethoxyimino)-2-(2-tritylaminothiazol-4-yl)acetamido]-3-chloromethyl-3-cephem- 4-carboxylate was dissolved in 200 ml of methylene chloride, and 1.78 g (10.3 mmol) of m-chloroperbenzoic acid was added under cooling with ice in 10 minutes. The mixture was further stirred for 20 minutes. To the reaction solution, 40 ml of a 10% sodium thiosulfate aqueous solution was added for extraction. Then, the organic layer was dried over anhydrous sodium sulfate and concentrated under reduced pressure to obtain a powder of the above-identified compound.

IR(KBr): 1795, 1720, 1680, 1500, 1365, 1300, 1250, 1170, 1140, 1050 cm-1

NMR(DMSO-$d_6$) δ: 1.36(9H, s), 1.45(6H, s), 3.9(2H, m), 4.55(2H, m), 5.1(1H, d, J=5 Hz), 6.0(1H, dd, J=5 & 9 Hz), 6.81(1H, s), 7.0(1H, s), 7.3(25H, brs), 8.15(1H, d, J=9 Hz), 8.7(1H, s)

(B) Benzhydryl 7-[(Z)-2-(1-tert-butoxycarbonyl-1-methylethoxyimino)-2-(2-tritylaminothiazol-4-yl)acetamido]-3-iodomethyl-3-cephem-4-carboxylate 1-oxide The compound obtained in (A) was dissolved in 200 ml of acetone, and 3.38 g (22.5 mmol) of sodium iodide was added. The mixture was stirred at room temperature for 30 minutes. To the reaction solution, 600 ml of ethyl acetate and 200 ml of a 10% sodium thiosulfate aqueous solution were added for extraction. Then, the organic layer was dried over anhydrous sodium sulfate and concentrated under reduced pressure. The residue was purified by slica gel flush column chromatography (ethyl acetate/n-hexane=½), and concentrated under reduced pressure. Then, diisopropyl ether was added thereto, and 7.0 g (yield: 63.0%) of a powder of the above-identified compound was collected by filtration.

IR(KBr): 1795, 1720, 1680, 1500, 1370, 1300, 1250, 1170, 1140, 1050 cm$^{-1}$

NMR(DMSO-$d_6$) δ: 1.35(9H, s), 1.45(6H, s), 3.95(2H, m), 4.45(2H, m), 5.1(1H, d, J=5 Hz), 6.0(1H, dd, J=5 & 9 Hz), 6.8(1H, s), 7.0(1H, s), 7.3(25H, brs), 8.15(1H, d, J=9 Hz), 8.7(1H, s)

(C) Benzhydryl 7-[(Z)-2-(1-tert-butoxycarbonyl-1-metylethoxyimino)-2-(2-tritylamiothiazol-4-yl)acetamido]-3-(5,6-dihydroxy-2-methyl-2-isoindolinium)methyl-3-cephem-4-carboxylate 1-oxide iodide To a suspension of 340 mg (2.1 mmol) of 5,6-dihydroxy-2-methylisoindoline and 25 ml of butyl acetate, 1.0 ml (4.1 mmol) of N,O-bistrimethylsilyl acetamide was added and dissolved under stirring at 5° C. for one hour. The solution was cooled to room temperature. Then, the solution was added at a stretch to a solution of 2 g (1.9 mmol) of the compound obtained in (B) and 20 ml of buthyl acetate. The mixture was stirred at room temperature for 6 hours, and then the solvent was removed under reduced pressure. The residue was purified by silica gel flush column chromatography (3 to 4% methanol-methylene chloride) to obtain 1.84 g (yield: 79.8%) of a powder of the above-identified compound.

IR(KBr): 1795, 1720, 1650, 1510, 1300, 1140 cm-1

(D) Benzhydryl 7-[(Z)-2-(1-tert-butoxycarbonyl-1-methylethoxyimino)-2-(2-tritylaminothiazol-4-yl) acetamido]-3-(5,6-dihydroxy-2-methyl-2-isoindolinium) methyl-3-cephem-4-carboxylate iodide 28 ml of acetone was added to 1.84 g (1.48 mmol) of the compound obtained in (C) and 1.23 g (7.4 mmol) of potassium iodide. Then, 0.26 ml (3.7 mmol) of acetyl chloride was dropwise added thereto at −20° C. The mixture was stirred at a temperature of from −20° to −10° C. for 2 hours, and then 600 mg of potassium iodide and 0.13 ml of acetyl chloride were added thereto. The mixture was further stirred at the same temperature for 4 hours. To the reaction solution, 100 ml of a cooled 10 % sodium metabisulfite aqueous solution-saturated sodium chloride aqueous solution (1/1) and 100 ml of methylene chloride were added for extraction. The organic layer was dried over anhydrous sodium sulfate and concentrated under reduced pressure to obtain a powder of the above-identified compound IR(KBr): 1790, 1720, 1680, 1510, 1360, 1300, 1220, 1140 cm$^{-1}$ (E) 7-[(Z)-2-(2-aminothiazol-4-yl)-2-(1-carboxy-1-methylethoxyimino)acetamido]-3-(5,6-dihydroxy-methyl-2-methyl-2-isoindolinium)methyl-3-cephem-4-carboxylate:

The compound obtained in (D) was dissolved in 18 ml of methylene chloride, and 1.8 ml of anisole was added. Then, 18 ml of cooled trifuloroacetic acid was added thereto under cooling with ice. The mixture was stirred at the same temperature for 5 hours. The solvent was distilled off under reduced pressure, then 20 ml of ethyl acetate was added thereto. The mixture was concentrated under reduced pressure. The operation was repeated twice. Then, 40 ml of diethyl ether was added to separate insoluble matters by filtration. The insoluble matters were suspended in 200 ml of water under stirring, and separated by filtration. Then, the aqueous layer was purified by reversed phase chromatography (Waters Pre Pack 500/C-18, 100 ml; H$_2$O, 300 ml, 2% and 3% tetrahydrofuran aqueous solutions, 500 ml, respectively), and after removal of the organic solvent under reduced pressure, freeze-dried to obtain 300 mg (yield: 32%) of the above-identified desired compound.

Melting point: 145° C. (decomposed)

IR(KBr): 1770, 1650, 1600, 1520, 1460, 1390, 1340, 1190, 1155 cm$^{-1}$

NMR(DMSO-d$_6$) δ: 1.48(6H, brs), 3.05(3H, brs), 5.12(1H, d, J=5 Hz), 5.75(1H, dd, J=5 & 9 Hz), 6.86(3H, brs), 9.8(1H, d, J=9 Hz)

EXAMPLE 8

(A) Benzhydryl 7-[(Z)-2-(benzhydryloxycarbonylmethoxyimino)-2-(2-tritylaminothiazol-4-yl)acetamido]-3-chloromethyl-3-cephem-4-carboxylate 1-oxide 23.4 g (22.3 mmol) of Benzhydryl-7-[(Z)-2-(benzhydryloxycarbonylmethoxyimino)-2-(2-tritylaminothiazol-4-yl)acetamido]-3-chloromethyl-3-cephem-4-carboxylate was dissolved in 500 ml of methylene chloride, and 4.8 g (22.3 mmol) of m-chloroperbenzoic acid was added under cooling with ice in 10 minutes. The mixture was further stirred for 20 minutes. To the reaction solution, 150 ml of a 10 % sodium thiosulfate aqueous solution was added for extraction. The organic layer was washed with a 5% sodium hydrogen carbonate aqueous solution, dried over anhydrous sodium sulfate and concentrated under reduced pressure to obtain a powder of the above-identified compound. The compound thus obtained was employed for the next reaction without purification IR(KBr): 1800, 1730, 1680, 1520, 1490, 1450, 1375, 1250, 1180, 1090, 1060, 1010, 750, 700 cm$^{-1}$ (B) Benzhydryl 7-[(Z)-2-(benzhydryloxycarbonyl-methoxyimino)-2-(2-tritylaminothiazol-4-yl)acetamido]-3-iodomethyl-3-cephem-4-carboxylate 1-oxide The compound obtained in (A) was dissoved in 380 ml of acetone, and 7.4 g (49 mmol) of sodium iodide was added thereto. The mixture was stirred at room temperature for 30 minutes. To the reaction solution, 300 ml of a 10% sodium thiosulfate aqueous solution and 1150 ml of ethyl acetate were added for extraction. Then, the organic layer was dried over anhydrous sodium sulfate and concentrated under reduced pressure. The residue was purified by silica gel flush column chromatography (ethyl acetate/n-hexane =1/1) to obtain 22.4 g of a powder of the above-identified compound (yield from the previous step: 86.7%).

IR(KBr): 1795, 1725, 1685, 1520, 1495, 1450, 1370, 1290, 1230, 1180, 1085, 1060, 750, 700 cm$^{-1}$

NMR(DMSO-d$_6$) δ: 3.9(2H, 5.08(1H, d, J=5 Hz), 5.93(1H, dd, J=5, 8 Hz), 6.87(1H, s), 6.92(1H, s), 7.0(1H, s), 7.35(36H, m), 8.85(2H, m)

(C) Benzhydryl 7-[(Z)-2-(benzhydryloxycarbonylmethoxyimino)-2-(2-tritylaminothiazol-4-yl)acetamido]-3-(5,6-dihydroxy-2-methyl-2-isoindolinium)methyl-3-cephem-4-carboxylate 1-oxide iodide To a suspension of 410 mg (2.48 mmol) of 5,6-dihydroxy-2-methylisoindoline and 20 ml of butyl acetate, 1.2 ml (4.96 mmol) of N,O-bistrimethylsilylacetamide was added and dissolved under stirring at 60° C. for one hour. The solution was cooled to room temperature, and then added at a stretch to a solution of 1.82 g (1.57 mmol) of the compound obtained in (B) and 20 ml of butyl acetate. The mixture was stirred at room temperature for one hour, and then the solvent was distilled off under reduced pressure. To the residue, 50 ml of diethyl ether was added. The insoluble matters were collected and purified by silica gel flush column chromatography (4% methanol-methylene chloride) to obtain 1.42 g (yield: 68%) of a powder of the above-identified compound.

IR(KBr): 1800, 1730, 1660, 1610, 1520, 1450, 1345, 1300, 1220, 1180, 1090, 1070, 1035, 750, 700 cm$^{-1}$ (D) Benzhydryl 7-[(Z)-2-(benzhydryloxycarbonylmethoxyimino)-2-(2-tritylaminothiazol-4-yl)acetamido]-3-(5,6-dihydroxy-2-methyl-2-isoindolinium)methyl-3-cephem-4-carboxylate iodide 23 ml of acetone was added to 1.42 g (1.01 mmol) of the compound obtained in (C) and 890 mg (5.04 mmol) of potassium iodide: Then, 0.19 ml ( 2.68 mmol) of acetyl chloride was dropwise added thereto at −20° C. The mixture was stirred at −10° C. One hour and two hours later, 890 mg (5.04 mmol) of potassium iodide and 0.19 ml (2.68 mmol) of acetyl chloride were added, respectively. The mixture was further stirred for 1 hour. To the reaction solution, 50 ml of cooled 10% sodium metabisulfite aqueous solution-saturated sodium chloride aqueous solution (1/1) and 100 ml of methylene chloride were added for extraction. The organic layer was washed with a saturated sodium chloride aqueous solution, then dried over anhydrous sodium sulfate and concentrated under reduced pressure to obtain a powder of the above-identified compound. (The compound thus obtained was employed for the next reaction without purification.)

IR(KBr): 1790, 1720, 1690, 1515, 1490, 1450, 1360, 1250, 1220, 1180, 1090, 1020, 750, 700 cm$^{-1}$ (E) 7-[(Z)-2-(2-aminothiazol-4-yl)-2-carboxymethoxyimino)acetamido]-3-(5,6-dihydroxy-2-methyl-2-isoindolinium)methyl-3-cephem-4-carboxylate The compound obtained in (D) was dissolved in 8 ml of methylene chloride, and 1.6 ml of anisole was added thereto. Then, a solution of 16 ml of trifluoroacetic acid and 8 ml of methylene chloride were dropwise added under cooling with ice in 30 minutes. The mixture was stirred at the same temperature for 3 hours. The solvent was distilled off under reduced pressure, and then 20 ml of 95% formic acid was added to the residue. The mixture was left to stand at 5° C. for 12 hours, and the solvent was distilled off under reduced pressure. 200 ml of water and 50 ml of ethyl acetate were added to the residue. The aqueous layer was again washed with 50 ml of ethyl acetate, then concentrated under reduced pressure by distilling off the organic solvent, and purified by reversed phase column chromatography (Waters Pre Pack 500/C-18, 100 ml ; 1% THF-H$_2$O). The organic solvent was distilled off under reduced pressure. The residue was freeze-dried to obtian 210 mg of the above-identified compound (yield from the previous step: 34%)

Melting point: 143° C. (decomposed)

IR(KBr): 1770, 1650, 1600, 1530, 1390, 1340, 1195, 1070, 1035 cm$^{-1}$
NMR(DMSO-d$_6$-D$_2$O)δ: 3.05(3H, brs), 4.5(2H, brs), 5.1(1H, d, J=5 Hz), 5.7(1H, d, J=5 Hz), 6.8(2H, brs), 6.83(1H, s)

EXAMPLE 9

(A) Benzhydryl 3-(5,6-dihydroxyisoindolin-2-yl)methyl-7-[(Z)-2-isopropoxyimino-2-(2-tritylaminothiazol-4-yl)acetamido]-3-cephem-4-carboxylate 1-oxide 2.0 g (2.26 mmol) of Benzhydryl 3-chloromethyl-7-[(Z)-2-isopropoxyimino-2-(2-tritylaminothiazol-4-yl)acetamido]-3-cephem-4-carboxylate 1-oxide was dissolved in 40 ml of acetone, and 750 mg (5 mmol) of sodium iodide was added thereto under cooling with ice. The mixture was stirred for 30 minutes. The reaction solution was concentrated under reduced pressure. To the residue, ethyl acetate and water were added. The organic layer was washed with a sodium metabisulfite aqueous solution and with a saturated sodium chloride aqueous solution, then dried over anhydrous sodium sulfate and concentrated under reduced pressure. The oily residue was dissolved in 10 ml of N,N-dimethylformamide, and 790 mg (3.4 mmol) of 5,6-dihydroxyisoindoline hydrobromide was added thereto, then 0.47 ml (3.38 mmol) of triethylamine was dropwise added at room temperature. The reaction solution was stirred at the same temperature for 2 hours, and then N,N-dimethylformamide was distilled off under reduced pressure. To the residue, chloroform and water were added. The organic layer was washed with water and with a saturated sodium chloride aqueous solution, then dried over anhydrous sodium sulfate and concentrated under reduced pressure. The residue was purified by silica gel flush column chromatography (5% methanol-chloroform) to obtain 1.74 g (yield: 78%) of the above-identified compound.

IR(KBr): 1790, 1660, 1490, 1290 cm$^{-1}$ (B) Benzhydryl 3-(5,6-dihydroxy-2-methyl-2-isoindolinium)methyl-7-[(Z)-2-isopropoxyimino-2-(2-tritylaminothiazol-4-yl)acetamido]-3-cephem-4-carboxylate 1-oxide iodide To 1.74 g (1.74 mmol) of the compound obtained in (A), 10 ml (160 mmol) of methyl iodide and 0.15 ml of N,N-dimethylformamide were added. The mixture was stirred at room temperature for 18 hours. The reaction solution was concentrated under reduced pressure. The residue was purified by silica gel flush column chromatography (4 to 5% methanol-chloroform) to obtain 1.0 g (yield: 50%) of the above-identified compound.

NMR(DMSO-d$_6$)δ: 1.25(6H, d, J=6.0 Hz), 2.87(2H, brs), 5.15(1H, d, J=4.0 Hz), 6.00(1H, m), 6.73(1H, s), 6.78(1H, s), 7.00(1H, s), 7.1–7.6(25H, brs), 8.75(1H, m), 9.28(1H, brs)

(C) 7-[(Z)-2-(2-aminothiazol-4-yl)-2-isopropoxyiminoacetamido]-3-(5,6-dihydroxy-2-methyl-2-isoindolinium) methyl-3-cephem-4-carboxylate 1.0 g (0.87 mmol) of the compound obtained in (B) was dissolved in 20 ml of acetone, then 1.45 g (8.7 mmol) of potassium iodide was added, and 0.31 ml (4.37 mmol) of acetyl chloride was dropwise added at −20° C. The reaction solution was stirred at −10° C. for 3 hours, and then poured into a 2% sodium metabisulfite aqueous solution cooled with ice, and the precipitates were collected by filtration. The precipitates were dissolved in chloroform, and the solution was washed with a saturated sodium chloride aqueous solution, then dried over anhydrous sodium sulfate and concentrated under reduced pressure.

The residue was dissolved in 2 ml of methylene chloride and 0.8 ml of anisole, and then 6 ml of trifluoroacetic acid was dropwise added thereto under cooling with ice. The reaction solution was stirred at the same temperature for 2 hours, and then concentrated under reduced pressure. To the residue, ethyl acetate and water were added. The aqueous layer was adjusted to pH 2.3, and subjected to reversed phase column chromatography (Waters Pre Pack 500/C-18; 2% tetrahydrofuran-water). The fraction containing the desired product was collected and concentrated under reduced pressure, and then freeze-dried to obtain 83.8 mg (yield: 17%) of the above-identified desired compound.

Melting point: 170° C. (decomposed)
IR(KBr): 1770, 1610, 1510, 1340 cm$^{-1}$
NMR(DMSO-d$_6$)δ: 1.25(6H, d, J=6.0 Hz), 5.10(1H, d, J=4.5 Hz), 5.70(1H, m), 6.71 (1H, s), 6.77(2H, s), 9.45(1H, d, J=9.0 Hz)

EXAMPLE 10

(A) Benzhydryl 7-[(Z)-2-(1-tert-butoxycarbonyl-1-cyclopropoxyimino)-2-(2-tritylaminothiazol-4-yl) acetamido]-3-iodomethyl-3-cephem-4-carboxylate 1-oxide 14.2 g (14.7 mmol) of benzhydryl 7-[(Z)-2-(1-tert-butoxycarbonyl-1-cyclopropoxyimino)-2-(2-tritylaminothiazol-4-yl)acetamido]-3-chloromethyl-3-cephem-4-carboxylate was dissolved in 280 ml of methylene chloride, and 2.98 g (14.7 mmol) of m-chloroperbenzoic acid was added thereto under cooling with ice. The mixture was stirred for 10 minutes. To the reaction solution, 60 ml of a 10% sodium thiosulfate aqueous solution was added. The aqueous solution was poured into a 5% sodium hydrogen carbonate aqueous solution, then extracted with methylene chloride and dried over anhydrous sodium sulfate. The residue obtained by the concentration under reduced pressure was dissolved in 300 ml of acetone, and then 4.4 g (29.4 mmol) of sodium iodide was added thereto at 0° C. The mixture was stirred at room temperature for 15 minutes. The reaction solution was washed with a sodium thiosulfate aqueous solution and with a saturated sodium chloride aqueous solution. Then the organic solvent layer was dried over anhydrous sodium sulfate. The residue obtained by the concentration under reduced pressure was subjected to silica gel flush column chromatography (ethyl acetate/n-hexane=½) to obtian 9.52 g (yield: 60%) of the above-identified compound.

(B) Benzhydryl 7-[(Z)-2-(1-tert-butoxycarbonyl-1-cyclopropoxyimino)-2-(2-tritylaminothizol-4-yl)acetamido]-3-(5,6-dihydroxyisoindoline-2-yl)methyl-3-cephem-4-carboxylate 1-oxide 2.5 g (2.3 mmol) of the compound obtained in (A) was dissolved in 25 ml of dimethylformamide, and 0.67 g (2.76 mmol) of 5,6-dihydroxyisoindoline hydrobromide and 0.77 ml (5.52 mmol) of triethylamine were added. The mixture was stirred at room temperature for 2 hours and concentrated under reduced pressure. The residue was subjected to silica gel flush column chromatography (ethyl acetate/n-hexane=3/1) to obtain 1.64 g (yield: 64%) of the above-identified compound as amorphous product.

NMR(DMSO-d$_6$)δ: 1.40(9H, s), 1.30(4H, m), 3.20–3.80(8H,m), 5.08(1H, d, J=4 Hz), 5.90(1H, m), 6.58(2H, s), 6.88(1H, s), 7.00(1H, s), 7.10–7.60(25H, m), 8.50–8.90(2H, m)

(C) Benzhydryl 7-[(Z)-2-(1-tert-butoxycarbonyl-1-cyclopropoxyimino)-2-(2-tritylaminothiazol-4-yl) acetamido]-3-(5,6-dihydroxy-2-methyl-2-isoindolinium) methyl-3-cephem-4-carboxylate 1-oxide iodide 1.64 g (1.48 mmol) of the compound obtained in (B) was dissolved in 16 ml (14.8 mmol) of methyl iodide. The mixture was left to stand at room temperature for 2.5 hours. The excess methyl iodide was distilled off under reduced pressure. Then, the residue was subjected to silca gel flush column chromatograpy (5% methanol-methylene chloride) to obtain 1.13 g (yield: 61%) of the above-identified compound as amorphous product.

NMR(DMSO-d$_6$)δ: 1.38(4H, m), 1.40(9H, s), 2.90(3H, bs), 4.10–4.90(8H, m), 5.22(1H, d, J=4 Hz), 6.00(1H, dd, J=4 & 7 Hz), 6.76(2H, s), 6.89(1H, s), 7.01(1H, s), 7.10–7.60(25H, m), 8.80(1H, bd, J=7 Hz), 9.28(1H, bs)

(D) Benzhydryl 7-[(Z)-2-(1-tert-butoxycarbonyl-1-cyclopropoxyimino)-2-(2-tritylaminothiazol-4-yl) acetamido]-3-(5,6-dihydroxy-2-methyl-2-isoindolinium) methyl-3-cephem-4-carboxylate iodide 1.1 g (0.88 mmol) of the compound obtained in (C) was dissolved in 20 ml of acetone, and 0.58 g (3.5 mmol) of potassium iodide was added. Then, 0.12 ml (1.75 mmol) of acetyl chloride was dropwise added thereto at −5° C. The mixture was stirred for 1 hour. To the reaction solution, a sodium metabisulfite aqueous solution was added, and the mixture was extracted with ethyl acetate. The extracted solution was dried over anhydrous sodium sulfate, and then the solvent was distilled off under reduced pressure. The residue was subjected again to the same reacting operation as above. Then, the same after-treatment as above was conducted to obtain 1.43 g of the above-identified compound as amorphous product. The compound thus obtained was employed for the next reaction without purification.

(E) 7-[(Z)-2-(2-aminothiazol-4-yl)-2-(1-carboxy-1-cyclopropoxyimino)acetamido]-3-(5,6-dihydroxy-2-methyl-2-isoindolinium)methyl-3-cephem-4-carboxylate 1.43 g of the compound obtained in (D) was dissolved in a solution of 2 ml of methylene chloride and 2 ml of anisole, and then 5 ml of trifluoroacetic acid was added thereto at −5° C. The mixture was stirred for 1 hour. The reaction solution was concentrated under reduced pressure, and the residue was dissolved in methylene chloride and extracted with water. The aqueous layer was subjected to reversed phase column chromatography (Waters Pre Pack 500/C-18: 2% tetrahydrofuran-water). The fraction containing the desired product was collected, concentrated under reduced pressure and then freeze-dried to obtain 41 mg of the above-identified desired product (yield from the previous step: 7.4%).

Melting point: 164° C. (decomposed)
IR(KBr): 3425, 1780, 1622 cm$^{-1}$

NMR(CF$_3$COOH)δ: 1.38(4H, m), 2.98(3H, bs), 3.28(2H, bs), 4.20–4.70(6H, m), 4.90(1H, d, J=4 Hz), 5.48(1H, dd, J=4 & 7 Hz), 6.50(2H, s), 6.89(1H, s), 8.08(1H, bd, J=7 Hz)

EXAMPLE 11

(A) Benzhydryl 7-[(Z)-2-(1-benzhydryloxycarbonyl-1-cyclobutoxyimino)-2-(2-tritylaminothiazol-4-yl)acetamido]-3-chloromethyl-3-cephem-4-carboxylate 1.82 g (2.62 mmol) of [(Z)-2-(1-benzhydryloxycarbonyl-1-cyclobutoxyimino)-2-(2-tritylaminothiazol-4-yl)acetic acid and 1.09 g (2.62 mmol) of benzhydryl 7-amino-3-chloromethyl-3-cephem-4-carboxylate were dissolved in 40 ml of methylene chloride, and then 1.06 ml (8.39 mmol) of N,N-dimethylaniline and 0.26 ml (2.75 mmol) of phosphorus oxychloride were dropwise added thereto under cooling with ice. The mixture was stirred at the same temperature for 4 hours. To the reaction solution, 30 ml of chloroform and 30 ml of water were added. The organic layer was washed with water and with a saturated sodium chloride aqueous solution, then dried over anhydrous sodium sulfate and concentrated to obtain a residue of the above-identified compound. The residue of the compound thus obtained was employed for the next reaction without purification.

(B) Benzhydryl 7[(Z)-2-(1-benzhydryloxycarbonyl-1-cyclobutoxyimino)-2-(2-tritylaminothiazol-4-yl)acetamido]-3-chloromethyl-3-cephem-4-carboxylate 1-oxide The residue obtained in (A) was dissolved in 50 ml of methylene chloride, and 620 mg (2.87 mmol) of m-chloroperbenzoic acid (purity: 80%) was added. The mixture was stirred for 20 minutes. To the reaction solution, 30 ml of methylene chloride and a 5% sodium bi-carbonate aqueous solution were added. Then, the organic layer was distributed and washed with water and with a saturated sodium chloride aqueous solution. Then, it was dried over anhydrous sodium sulfate, and concentrated to obtain a residue of the above-identified compound. The residue of the compound thus obtained was employed for the next reaction without purification.

(C) Benzhydryl 7-[(Z)-2-(1-benzhydryloxycarbonyl-1-cyclobutoxyimino)-2-(2-tritylaminothiazl-4-yl) acetamido]-3-iodomethyl-3-cephem-4-carboxylate 1-oxide The residue obtained in (B) was dissolved in 40 ml of acetone, and 870 mg (2.62 mmol) of sodium iodide was added. The mixture was stirred at room temperatrue for 30 minutes. To the reaction solution, 120 ml of ethyl acetate and 20 ml of 5% sodium thiosulfate were added for extraction. The organic layer was washed with water and with a saturated sodium chloride aqueous solution, then dried over anhydrous sodium sulfate, and concentrated under reduced pressure. The concentrated residue was subjected to silica gel flush column chromatography (ethyl acetate/n-hexane=½). The fraction containing the desired product was collected and concentrated under reduced pressure. To the residue, isopropyl ether was added to obtain 2.63 g of a powder of the above-identified compound (yield from A: 83.7%).

IR(KBr): 1800, 1730, 1690, 1520, 1495, 1450, 1370cm$^{-1}$

NMR(DMSO-d$_6$)δ: 2.00(2H, m), 2.45(4H, m), 3.90(2H, m), 4.25(2H, ABq, J=9 Hz), 5.10(1H, d, J=5 Hz) 5.95(1H, dd, J=5 & 9 Hz), 6.78(1H, s), 6.85(1H, s), 7.00(1H, s), 7.30(35H, m), 8.87(1H, d, J=9 Hz), 8.82(1H, bs)

(D) Benzhydryl 7-[(Z)-2-(1-benzhydryloxycarbonyl-1-cyclobutoxyimino)-2-(2-tritylaminothiazol-4-yl)acetamido]-3-(5,6-dihydroxy-2-methyl-2-isoindolinium)methyl-3-cephem-4-carboxylate 1-oxide iodide 464 mg (2.80 mmol) of 5,6-dihydroxy-2-methylisoindoline was suspended in 26 ml of butyl acetate, and 1.4 ml (5.62 mmol) of N,O-bistrimethylsilylacetamide was added. The mixture was stirred at 50° C. for 30 minutes, then cooled with ice. The solution was added at a stretch to 26 ml of a butyl acetate solution containing 2.59 g (2.16 mmol) of the powder obtained in (C) under cooling with ice. The mixture was stirred at the same temperature for 3 hours. The reaction solution was subjected to slica gel flush column chromatography (4% methanol-methylene chloride) as it was to obtain 1.60 g (yield: 54.3%) of a powder of the above-identified compound IR(KBr): 1790, 1730, 1660, 1520, 1450, 1390, 1350, 1300, 1250, 1150 cm$^{-1}$ (E) Benzhydryl 7-[(Z)-2-(1-benzhydryloxycarbonyl-1-cyclobutoxyimino)-2-(2-tritylaminothiazol-4-yl)acetamido]-3-(5,6-dihydroxy-2-methyl-2-isoindolinium)methyl-3-cephem-4-carboxylate iodide 1.60 g (1.17 mmol) of the powder obtained in (D) was dissloved in 35 ml of acetone, 974 mg (5.85 mmol) of potassium iodide was added, and 0.21 ml (2.93 mmol) of acetyl chloride was dropwise added at −20° C. The mixture was stirred for 1 hour, and then 974 mg (5.85 mmol) of potassium iodide and 0.21 ml (2.93 mmol) of acetyl chloride were added thereto. The mixture was stirred for 1 hour. To the reaction solution, 140 ml of methylene chloride and 35 ml of a 5% sodium metabisulfite aqueous solution were added for extraction. The organic layer was washed with water and with a saturated sodium chloride aqueous solution, then dried over anhydrous sodium sulfate, and concentrated to obtain a residue of the above-identified compound. The residue thus obtained was employed for the next reaction without purification.

(F) 7-[(Z)-2-(2-aminothiazol-4-yl)-2-(1-carboxy-1-cyclobutoxyimino)acetamido]-3-(5,6-dihydroxy-2-methyl-2-isoindolinium)methyl-3-cephem-4-carboxylate The residue obtained in (E) was dissolved in 1.6 ml of anisole and 13 ml of methylene chloride, and a solution of 16 ml of trifluoroacetic acid and 3 ml of methylene chloride were dropwise added under cooling with ice in 20 minutes. The mixture was stirred at the same temperature for 1 hour, and then the solvent was distilled off under reduced pressure. To the residue, 30 ml of ethyl acetate was added, the mixture was concentrated under reduced pressure (this operation was repeated twice). To the residue, 40 ml of ethyl acetate was added, and insoluble matters were collected by filtration. The insoluble matters were dissolved in 35 ml of 95% formic acid. The solution was stirred at 40° C. for 1 hour, and then concentrated under reduced pressure. To the residue, 40 ml of ethyl acetate was added, and the insoluble matters were collected by filtration. To the insoluble matters, 100 ml of water was added, the mixture was stirred for 30 minutes. Then, the insoluble matters were separated by filtration, and the filtrate was purified by reversed phase column chromatography (ODS, 10 ml; after adsorption and washing with water, 2% tetrahydrofuran-water). The solvent was distilled off under reduced pressure. Then, the residue was freeze-dried to obtain 46 mg of the above-identified compound (yield from E: 6.4%).

Melting point : 157° C. (decomposed)

IR(KBr): 1775, 1660, 1620, 1540, 1400, 1350 cm$^{-1}$

NMR(DMSO-d$_6$)δ: 1.90(2H, m), 2.40(4H, m), 3.05(3H, bs), 5.15(1H, d, J=5 Hz), 5.80(1H, dd, J=5 & 9 Hz), 6.90(3H, s), 9.70(1H, d, J=9 Hz)

EXAMPLE 12

(A) Benzhydryl 7-[(Z)-2-(1-benzhydryloxycarbonyl-1-cyclopentyloxyimino)-2-(2-tritylaminothiazol-4-yl) acetamido]-3-(5,6-dihydroxy-2-methyl-2-isoindolinium)methyl-3-cephem-4-carboxylate 1-oxide iodide 517 mg (3.13 mmol) of 5,6-dihydroxy-2-methylisoindoline was suspended in 26 ml of butyl acetate, and 1.5 ml (6.26 mmol) of N,O-bistrimetylsilylacetamide was added. The mixture was stirred at 50° C. for 30 minutes and then cooled with ice. The solution was added at a stretch under cooling with ice, to 26 ml of a butyl acetate solution containing 2.92 g (2.41 mmol) of benzhydryl 7-[(Z)-2-(1-benzhydryloxycarbonyl-1-cyclopentyloxyimino)-2-(2-tritylaminothiazol-4-yl) acetamido]-3-iodomethyl-3-cephem-4-carboxylate 1-oxide obtained by the same operations as in (A), (B) and (C) of EXAMPLE 11. The mixture was stirred at the same temperature for 3 hours. The reaction solution was subjected to slica gel flush colum chromatograpy (5% methanol-methylene chloride) as it was to obtain 1.48 g (yield: 44.6%) of a powder of the above-identified compound.

IR(KBr): 1800, 1730, 1670, 1520, 1450, 1300, 1250, 1170, 1060, 1030, 845, 750, 700 cm$^{-1}$ (B) Benzhydryl 7-[(Z)-2-(1-benzhydryloxycarbonyl-1-cyclopentyloxyimino)-2-(2-tritylaminothiazol-4-yl) acetamido]-3-(5,6-dihydroxy-2-methyl-2-isoindolinium) methyl-3-cephem-4-carboxylate iodide 1.48 g (1.07 mmol) of the powder obtained in (A) was dissolved in 30 ml of acetone, and 890 mg (5.37 mmol) of potassium iodide was added, and 0.19 ml (2.69 mmol) of acetyl chloride was dropwise added at −20° C. The mixture was stirred for 1 hour. Then, 890 mg (5.37 mmol) of potassium iodide and 0.19 ml (2.69 mmol) were further added thereto. The mixture was stirred for 1 hour. To the reaction solution, 120 ml of methylene chloride and 30 ml of a 5% sodium metabisulfite aqueous solution were added for extraction. The organic layer was washed with water and with a saturated sodium chloride aqueous solution, then dried over anhydrous sodium sulfate and concentrated to obtain a residue of the above-identified compound. The residue thus obtained was employed for the next reaction without purification.

IR(KBr): 1790, 1730, 1680, 1520, 1495, 1450, 1180, 1000, 750, 700 cm$^{-1}$ (C)
7-[(Z)-2-(2-aminothiazol-4-yl)-2-(1-carboxy-1-cyclopentyloxyimino)acetamido]-3-(5,6-dihydroxy-2-methyl-2-isoindolinium)methyl-3-cephem-4-carboxylate The residue obtained in (B) was dissolved in 1.5 ml of anisole and 10 ml of methylene chloride. A solution of 15 ml of trifluoroacetic acid and 5 ml of methylene chloride was dropwise added thereto under cooling with ice in 15 minutes. The mixture was stirred at the same temperature for 1 hour, and then the solvent was distilled off under reduced pressure To the residue, 30 ml of ethyl acetate was added, and the mixture was concentrated under reduced pressure (the operation was repeated twice). To the residue, 40 ml of ethyl acetate was added, and insoluble matters were collected by filtration. The insoluble matters were dissolved in 30 ml of 95% formic acid. The solution was stirred at 40° C. for 1 hour, and then concentrated. To the residue, 40 ml of ethyl acetate was added, and insoluble matters were collected by filtration. To the insoluble matters, 100 ml of water was added. The mixture was stirred for 30 minutes, and then the insoluble matters were separated by filtration. The filtrate was purified by reversed phase column chromatograpy (ODS, 100 ml; after adsorption and washing with water, 3% tetrahydrofuran-water). The organic solvent was distilled off under reduced pressure. The residue was freeze-dried to obtain 75 mg of the above-identified compound (yield from A: 10.6%).

Melting point: 165° C. (decomposed)
IR(KBr): 1775, 1660, 1620, 1540, 1400, 1350, 1200, 1000 cm$^{-1}$
NMR(DMSO-d$_6$)$\delta$: 1.70(4H, m), 2.10(4H, m), 3.05(3H, bs), 5.15(1H, d, J=5 Hz), 5.75(1H, dd, J=5 & 9 Hz), 6.80(3H, s), 9.70(1H, d, J=9 Hz)

EXAMPLE 13

(A) Benzhydryl 7-[(Z)-2-cyclopentyloxyimino-2-(2-tritylaminothiazol-4-yl)acetamido]-3-(5,6-dihydroxyisoindoline-2-yl)methyl-3-cephem-4-carboxylate 1-oxide 2.64 g (2.65 mmol) of benzhydryl 7-[(Z)-2-cyclopentyloxyimino)-2-(2-tritylaminothiazol-4-yl) acetamido]-3-iodomethyl-3-cephem-4-carboxylate 1-oxide was dissolved in 26.4 ml of N,N-dimethylformamide, and 0.64 g (2.65 mmol) of 5,6-dihydroxyisoindoline hydrobromide was added, then 0.74 ml (5.30 mmol) of triethylamine was dropwise added at room temperature. The reaction solution was stirred for 1 hour, then N,N-dimethylformamide was distilled off under reduced pressure. The residue was purified by silica gel column chromatography (ethyl acetate/n-hexane=3/1) to obtain 1.42 g (yield: 52%) of the above-identified compound.

NMR(DMSO-d$_6$)$\delta$: 1.70(8H, m), 3.10-4.10(8H, m), 4.70(1H, m), 5.10(1H, d, J=5 Hz), 5.90(1H, dd, J=5 & 8 Hz), 6.60(2H, bs), 6.83(1H, s), 7.01(1H, s), 7.10-7.80(25H, m), 8.56(1H, bd, J=8 Hz)

(B) Benzhydryl 7-[(Z)-2-cyclopentyloxyimino-2-(2-tritylaminothiazol-4-yl)acetamido]-3-(5,6-dihydroxy-2-methyl-2-isoindoliniun)methyl-3-cephem-4-carboxylate 1-oxide iodide 1.42 g (1.38 mmol) of the compound obtained in (A) was dissolved in 14 ml (225 mmol) of methyl iodide. The solution was left to stand at room temperature for 16 hours. The reaction solution was concentrated under reduced pressure. The residue was purified by silica gel column chromatography (5% methanol-methylene chloride) to obtain 1.25 g (yield: 77%) of the above-identified compound.

NMR(DMSO-d$_6$)$\delta$: 1.70(8H, m), 2.90(3H, bs), 3.42(2H, bs), 4.20(1H, m), 4.60(6H, m), 5.20(1H, d, J=5 Hz), 5.98(1H, dd, J=5 & 7 Hz), 6.77(2H, bs), 6.80(1H, s), 7.03(1H, s), 7.10-7.80(25H, m), 8.86(1H, bd, J=7 Hz)

(C) Benzhydryl 7-[(Z)-2-cyclopentyloxyimino)-2-(2-tritylaminothiazol-4-yl)acetamido]-3-(5,6-dihydroxy-2-methyl-isoindolinium)methyl-3-cephem-4-carboxylate iodide 1.25 g (1.07 mmol) of the compound obtained in (B) was dissolved in 25 ml (1.07 mmol) of acetone, then 0.71 g (4.28 mmol) of potassium iodide was added and 0.15 ml (2.14 mmol) of acetyl chloride was dropwise added at 0° C. The reaction solution was stirred at 0° C. for 1 hour, then poured into a sodium metabisulfite aqueous solution which was cooled with ice and extracted with ethyl acetate to obtain a crude residue of the above-identified compound. The crude residue thus obtained was employed for the next step without purification.

(D)
7-[(Z)-2-(2-aminothiazol-4-yl)-2-cyclopentyloxyiminoacetamido]-3-(5,6-dihydroxy-2-methyl-2-isoindolinium)methyl-3-cephem-4-carboxylate The residue obtained in (C) was dissolved in 2 ml of methylene chloride and 2 ml of anisole, then 5 ml of trifluoroacetic acid was dropwise added under cooling with ice. The reaction solution was stirred for 1 hour and then concentrated under reduced pressure. To the residue, ethyl acetate and water were added. The aqueous layer was concentrated and then purified by ODS column chromatography (Bandapack: 30% methanol-water) to obtain 196 mg of the above-identified compound (yield from the previous step: 30%).

Melting point: 159° C. (decomposed)
IR(KBr): 3425, 1775, 1619 cm$^{-1}$
NMR(CF$_3$COOH)$\delta$: 1.40(4H, m), 1.51(4H, m), 2.97(3H, bs) 3.40(2H, bs), 4.47(7H, m), 4.90(1H, d, J=5 Hz), 5.48(1H, dd, J=5 & 7 Hz), 6.49(2H, bs), 6.89(1H, s), 8.11(1H, bd, J=7 Hz)

REFERENCE EXAMPLE

Benzhydryl 3-chloromethyl-7-[(Z)-2-methoxyimino-2-(2-tritylaminothiazol-4-yl)acetamido]-3-cephem-4-carboxylate 1-oxide and 2-methylisoindoline were employed as starting materials, and, in the same manner as in Example 1, 7-[(Z)-2-(2-aminothiazol-4-yl)-2-methoxyiminoacetamido]-3-(2-methyl-2-isoindolinium)methyl-3-cephem-4-carboxylate was obtained.

Melting point : 150° C. (decomposed)
IR(KBr): 1770, 1660, 1620, 1530, 1345, 1030 cm$^{-1}$
NMR(D$_2$O)$\delta$: 3.23(2H, s), 3.98(3H, s), 5.16(1H, d, J=4.5 Hz), 5.76(1H, d, J=4.5 Hz), 6.93(1H, s), 7.38(4H, bs)

The compounds of the present invention exhibit strong antibacterial activities against sensitive and resistant Gram-positive bacteria and Gram-negative bacteria, particularly against resistant Pseudomonas aeruginosa, Pseudomonas cepacia and Acinetobacter calcoaceticus. Thus, the compounds of the present invention are expected to be effective antibacterial agents for the treatment of diseases caused by bacterial infection. Among them, the compounds having a 2-(2-aminothiazol-4-yl)-2-substituted-oxyiminoacetyl group as a side chain at the 7-position and a 2-methyl-5,6-disubstituted isoindolinium methyl group, at the 3-position [the compounds of Examples 3D, 4D, 5D, 7E, 8E, 9C, 10E, 12C and 13D] exhibit particularly strong antibacterial activities.

We claim:

1. A compound having the formula:

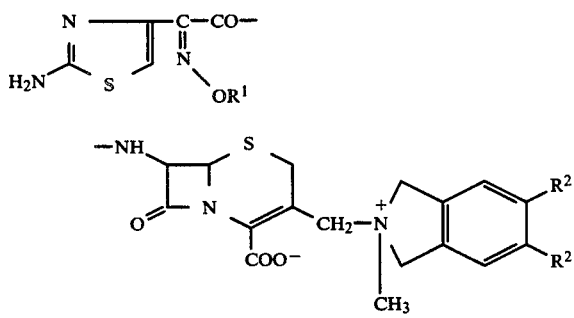

wherein $R^1$ is a straight chain, branched chain or cylic lower alkyl group which may be substituted by a carboxyl group, and $R^2$ is a hydroxy group or an acetoxy group; or a pharmaceutically acceptable salt, physiologically hydrolyzable ester or solvate thereof.

2. The compound according to claim 1, wherein $R^1$ is methyl, ethyl, n-propyl, isopropyl, n-butyl, carboxymethyl, 1-carboxy-1-methylethyl, cyclopropyl, cyclobutyl, cyclopentyl, cyclohexyl, 1-carboxy-1-cyclopropyl, 1-carboxy-1-cyclobutyl, 1-carboxy-1-cyclopentyl or 1-carboxy-1-cyclohexyl.

3. The compound according to claim 1, wherein $R^1$ is a straight chain, branched chain or cyclic lower alkyl group.

4. The compound according to claim 1, wherein $R^1$ is a straight chain, branched chain or cyclic lower alkyl group substituted by a carboxyl group.

5. The compound according to claim 4, wherein $R^1$ is a cyclic lower alkyl group substituted by a carboxyl group.

6. The compound according to claim 1, which is
7-[(Z)-2-(2-aminothiazol-4-yl)-2-methoxyiminoacetamido]-3-(5,6-diacetoxy-2-methyl-2-isoindolinium)methyl-3-cephem-4-carboxylate,
7-[(Z)-2-(2-aminothiazol-4-yl)-2-methoxyiminoacetamido]-3-(5,6-dihydroxy-2-methyl-2-isoindolinium)methyl-3-cephem-4-carboxylate,
7-[(Z)-2-(2-aminothiazol-4-yl)-2-ethoxyiminoacetamido]-3-(5,6-dihydroxy-2-methyl-2-isoindolinium)methyl-3-cephem-4-carboxylate,
7-[(Z)-2-(2-aminothiazol-4-yl)-2-ethoxyiminoacetamido]-3-(5,6-diacetoxy-2-methyl-2-isoindolinium)methyl-3-cephem-4-carboxylate,
7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate,
7-[(Z)-2-(2-aminothiazol-4-yl)-2-(carboxymethoxyimino) acetamido]-3-(5,6-dihydroxy-2-methyl-2-isoindolinium) methyl-3-cephem-4-carboxylate,
7-[(Z)-2-(2-aminothiazol-4-yl)-2-isopropoxyiminoacetamido]-3-(5,6-dihydroxy-2-methyl-2-isoindolinium) methyl-3-cephem-4-carboxylate,
7-[(Z)-2-(2-aminothiazol-4-yl)-2-(1-carboxy-1-cyclopropoxyimino)acetamido]-3-(5,6-dihydroxy-2-methyl-2-isoindolinium)methyl-3-cephem-4-carboxylate,
7-[(Z)-2-(2-aminothiazol-4-yl)-2-(1-carboxy-1-cyclobutoxyimino)acetamido]-3-(5,6-dihydroxy-2-methyl-2-isoindolinium)methyl-3-cephem-4-carboxylate,
7-[(Z)-2-(2-aminothiazol-4-yl)-2-(1-carboxy-1-cyclopentyloxyimino)acetamido]-3-(5,6-dihydroxy-2-methyl-2-isoindolinium)methyl-3-cephem-4-carboxylate or
7-[(Z)-2-aminothiazol-4-yl)-2-cyclopentyloxyiminoacetamido] -3-(5,6-dihydroxy-2-methyl-2-isoindolinium) methyl-3-cephem-4-carboxylate.

7. An antibacterial agent comprising an antibacterially effective amount of a compound having the formula:

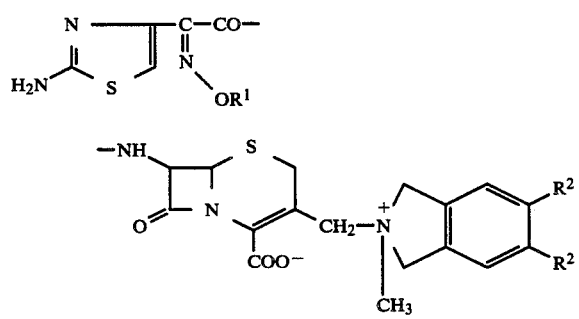

wherein $R^1$ is a straight chain, branched chain or cyclic lower alkyl group which may be substituted by a carboxyl group, and $R^2$ is a hydroxy group or an acetoxy group; or a pharmaceutically acceptable salt, physiologically hydrolyzable ester or solvate thereof, and a pharmaceutically acceptable carrier.

8. A method for treating disease caused by the infection of bacteria which comprises administering to a subject in need of treatment an antibacterially effective amount of the compound according to claim 1.

* * * * *